US 8,679,523 B2

(12) United States Patent
Gibbins et al.

(10) Patent No.: US 8,679,523 B2
(45) Date of Patent: Mar. 25, 2014

(54) OXYGEN-DELIVERY CLOSED CELL FOAM MATRIX FOR WOUND TREATMENT

(75) Inventors: Bruce L. Gibbins, Lake Oswego, OR (US); Lance D. Hopman, Aloha, OR (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 0 days.

(21) Appl. No.: 09/752,939

(22) Filed: Dec. 29, 2000

(65) Prior Publication Data

US 2001/0041188 A1   Nov. 15, 2001

Related U.S. Application Data

(60) Provisional application No. 60/174,024, filed on Dec. 30, 1999.

(51) Int. Cl.
*A61F 13/00* (2006.01)
*A61F 13/02* (2006.01)
*A61K 9/70* (2006.01)
*A61K 9/14* (2006.01)
*A61L 15/00* (2006.01)
*A61L 15/16* (2006.01)

(52) U.S. Cl.
USPC ........... 424/443; 424/444; 424/445; 424/446; 424/447; 424/448; 424/449; 424/484; 424/485; 424/486; 424/487; 424/488

(58) Field of Classification Search
USPC ......... 424/443, 78.06, 484–489, 449; 602/41, 602/43
See application file for complete search history.

(56) References Cited

U.S. PATENT DOCUMENTS

| 2,396,515 | A |   | 3/1946  | Kreidl et al. |
|-----------|---|---|---------|---------------|
| 2,934,066 | A |   | 4/1960  | Stowasser et al. |
| 3,092,552 | A |   | 6/1963  | Romans |
| 3,152,094 | A |   | 10/1964 | Erner et al. |
| 3,152,904 | A |   | 10/1964 | Sorensen et al. |
| 3,157,524 | A |   | 11/1964 | Artandi |
| 3,485,658 | A |   | 12/1969 | Iler |
| 3,511,764 | A | * | 5/1970  | Marans et al. ............... 521/50.5 |
| 3,624,835 | A |   | 11/1971 | Wyatt |
| 3,645,835 | A |   | 2/1972  | Hodgson |

(Continued)

FOREIGN PATENT DOCUMENTS

DE   19631421 A1   2/1998
EP   0 072 251 A2   2/1983

(Continued)

OTHER PUBLICATIONS

Aubry "Chemical Source of Singlet Oxygen Peroxidation of Water-Soluble Singlet Oxygen Carriers with the Hydrogen Peroxide-Molybdate", J. Org. Chem. 1989, 54, 726-728.*

(Continued)

*Primary Examiner* — Isis Ghali
(74) *Attorney, Agent, or Firm* — Dority & Manning, P.A.

(57) ABSTRACT

The present invention comprises methods and compositions for delivery devices. More particularly, the present invention comprises methods and compositions for devices comprising a matrix comprising a polymer network and a non-gellable polysaccharide having oxygen and optionally active agents incorporated therein. The matrix may be formed into any desired shape for treatment of compromised tissue or for delivery of oxygen to a localized environment.

13 Claims, 4 Drawing Sheets

(56) References Cited

U.S. PATENT DOCUMENTS

| | | |
|---|---|---|
| 3,647,439 A | 3/1972 | Bass |
| 3,846,236 A | 11/1974 | Updike et al. |
| 3,933,507 A | 1/1976 | Von Konig et al. |
| 3,969,498 A | 7/1976 | Catania et al. |
| 3,996,141 A | 12/1976 | Updike |
| 4,113,658 A | 9/1978 | Geus |
| 4,130,517 A | 12/1978 | Lundberg et al. |
| 4,136,177 A | 1/1979 | Lin et al. |
| 4,136,178 A | 1/1979 | Lin et al. |
| 4,260,677 A | 4/1981 | Winslow et al. |
| 4,306,551 A | 12/1981 | Hymes et al. |
| 4,310,509 A | 1/1982 | Berglund et al. |
| 4,320,201 A | 3/1982 | Berg et al. |
| 4,328,799 A | 5/1982 | LoPiano |
| 4,340,043 A | 7/1982 | Seymour |
| 4,364,929 A | 12/1982 | Sasmor et al. |
| 4,393,048 A | 7/1983 | Mason, Jr. et al. |
| 4,474,571 A | 10/1984 | Lasley |
| 4,483,688 A | 11/1984 | Akiyama |
| 4,529,623 A | 7/1985 | Maggs |
| 4,604,384 A | 8/1986 | Smith et al. |
| 4,608,041 A | 8/1986 | Nielsen |
| 4,612,337 A | 9/1986 | Fox, Jr. et al. |
| 4,613,628 A * | 9/1986 | Hoshino et al. ................ 521/72 |
| 4,624,656 A | 11/1986 | Clark et al. |
| 4,686,211 A | 8/1987 | Hara et al. |
| 4,708,821 A | 11/1987 | Shimokawa et al. |
| 4,721,724 A | 1/1988 | Stettendorf et al. |
| 4,747,847 A | 5/1988 | Magruder et al. |
| 4,782,819 A | 11/1988 | Adair |
| 4,801,291 A | 1/1989 | Loori |
| 4,902,503 A | 2/1990 | Umemura et al. |
| 4,915,694 A | 4/1990 | Yamamoto et al. |
| 4,969,881 A | 11/1990 | Viesturs |
| 5,023,082 A | 6/1991 | Friedman et al. |
| 5,049,139 A | 9/1991 | Gilchrist |
| 5,076,265 A | 12/1991 | Wokalek |
| 5,086,620 A | 2/1992 | Spears |
| 5,091,171 A | 2/1992 | Yu et al. |
| 5,100,668 A | 3/1992 | Edelman et al. |
| 5,128,326 A | 7/1992 | Balazs et al. |
| 5,149,524 A | 9/1992 | Sherba et al. |
| 5,151,271 A | 9/1992 | Otsuka et al. |
| 5,158,772 A | 10/1992 | Davis |
| 5,175,229 A | 12/1992 | Braatz et al. |
| 5,181,914 A | 1/1993 | Zook |
| 5,196,190 A | 3/1993 | Nangia et al. |
| 5,236,421 A | 8/1993 | Becher |
| 5,270,358 A | 12/1993 | Asmus |
| 5,326,567 A | 7/1994 | Capelli |
| 5,342,528 A | 8/1994 | Adachi et al. |
| 5,354,862 A | 10/1994 | Hsu |
| 5,407,685 A | 4/1995 | Malchesky et al. |
| 5,429,591 A | 7/1995 | Yamamoto et al. |
| 5,432,077 A | 7/1995 | Farrah |
| 5,447,492 A | 9/1995 | Cartmell et al. |
| 5,453,401 A | 9/1995 | Grivna et al. |
| 5,454,886 A | 10/1995 | Burrell et al. |
| 5,464,610 A | 11/1995 | Hayes, Jr. et al. |
| 5,470,585 A | 11/1995 | Gilchrist |
| 5,503,840 A | 4/1996 | Jacobson et al. |
| 5,508,038 A | 4/1996 | Wang et al. |
| 5,508,417 A | 4/1996 | Osei-Gyimah et al. |
| 5,516,502 A | 5/1996 | Dickerson |
| 5,527,534 A | 6/1996 | Myhling |
| 5,567,495 A | 10/1996 | Modak et al. |
| 5,569,207 A | 10/1996 | Gisselberg et al. |
| 5,593,683 A | 1/1997 | Viegas et al. |
| 5,599,296 A | 2/1997 | Spears |
| 5,603,946 A | 2/1997 | Constantine |
| 5,614,568 A | 3/1997 | Mawatari et al. |
| 5,660,854 A | 8/1997 | Haynes et al. |
| 5,681,579 A | 10/1997 | Freeman |
| 5,683,713 A | 11/1997 | Blank et al. |
| 5,693,624 A | 12/1997 | Hardy et al. |
| 5,695,777 A | 12/1997 | Donovan et al. |
| 5,709,870 A | 1/1998 | Yoshimura et al. |
| 5,725,491 A | 3/1998 | Tipton et al. |
| 5,735,251 A | 4/1998 | Hyodo et al. |
| 5,736,582 A | 4/1998 | Devillez |
| 5,744,151 A | 4/1998 | Capelli |
| 5,753,251 A | 5/1998 | Burrell et al. |
| 5,792,090 A * | 8/1998 | Ladin .............. 602/48 |
| 5,804,213 A | 9/1998 | Rolf |
| 5,820,918 A | 10/1998 | Ronan et al. |
| 5,830,496 A | 11/1998 | Freeman |
| 5,833,665 A | 11/1998 | Bootman et al. |
| 5,840,283 A | 11/1998 | Sorenson et al. |
| 5,853,742 A | 12/1998 | Bartolone et al. |
| 5,855,570 A | 1/1999 | Scherson et al. |
| 5,863,548 A | 1/1999 | Elder |
| 5,863,864 A | 1/1999 | Plath et al. |
| 5,869,073 A | 2/1999 | Sawan et al. |
| 5,908,693 A | 6/1999 | Delgado et al. |
| 5,927,317 A | 7/1999 | Hsia |
| 5,928,174 A * | 7/1999 | Gibbins .............. 602/41 |
| 5,951,458 A | 9/1999 | Hastings et al. |
| 5,961,996 A | 10/1999 | Garson et al. |
| 5,965,204 A | 10/1999 | Sodervall et al. |
| 5,972,317 A | 10/1999 | Sorenson et al. |
| 5,993,790 A | 11/1999 | Strauss |
| 6,000,403 A | 12/1999 | Cantwell |
| 6,004,667 A | 12/1999 | Sakurada et al. |
| 6,011,194 A | 1/2000 | Buglino et al. |
| 6,014,585 A | 1/2000 | Stoddard |
| 6,042,845 A | 3/2000 | Sun et al. |
| 6,051,614 A | 4/2000 | Hirai et al. |
| 6,099,805 A | 8/2000 | Hartlove |
| 6,103,868 A | 8/2000 | Heath et al. |
| 6,110,447 A | 8/2000 | Ramin et al. |
| 6,113,287 A | 9/2000 | Merz et al. |
| 6,143,794 A | 11/2000 | Chaudhuri et al. |
| 6,159,977 A | 12/2000 | Reeves |
| 6,187,290 B1 * | 2/2001 | Gilchrist et al. .............. 424/45 |
| 6,191,339 B1 | 2/2001 | Gueret |
| 6,201,164 B1 | 3/2001 | Wulff et al. |
| 6,214,360 B1 | 4/2001 | Richter et al. |
| 6,224,622 B1 | 5/2001 | Kotzev |
| 6,231,840 B1 | 5/2001 | Buck |
| 6,235,964 B1 | 5/2001 | Kadash et al. |
| 6,248,342 B1 | 6/2001 | Trogolo et al. |
| 6,264,927 B1 | 7/2001 | Monahan |
| 6,270,811 B1 | 8/2001 | Fregonese |
| 6,316,084 B1 | 11/2001 | Claus et al. |
| 6,326,524 B1 | 12/2001 | Fattman et al. |
| 6,355,858 B1 | 3/2002 | Gibbins |
| 6,468,989 B1 | 10/2002 | Chang et al. |
| 6,471,982 B1 | 10/2002 | Lydon et al. |
| 6,530,895 B1 | 3/2003 | Keirn |
| 6,605,751 B1 | 8/2003 | Gibbins et al. |
| 6,669,981 B2 | 12/2003 | Parsons et al. |
| 6,716,895 B1 | 4/2004 | Terry |
| 6,897,349 B2 | 5/2005 | Gibbins et al. |
| 6,921,529 B2 | 7/2005 | Maley |
| 7,129,389 B1 | 10/2006 | Watson |
| 7,160,553 B2 | 1/2007 | Gibbins et al. |
| 7,166,330 B2 | 1/2007 | Takahashi et al. |
| 7,189,410 B1 | 3/2007 | Drohan et al. |
| 7,576,255 B2 | 8/2009 | Gibbins et al. |
| 2001/0026810 A1 | 10/2001 | McGhee et al. |
| 2002/0001604 A1 | 1/2002 | Shigeru et al. |
| 2002/0042587 A1 * | 4/2002 | Murdock .............. 604/20 |
| 2002/0073891 A1 | 6/2002 | Parsons et al. |
| 2002/0082340 A1 | 6/2002 | Hanke et al. |
| 2003/0041188 A1 | 2/2003 | Han et al. |
| 2003/0083610 A1 | 5/2003 | McGrath et al. |
| 2003/0093057 A1 | 5/2003 | Zhang et al. |
| 2003/0186955 A1 | 10/2003 | Vange et al. |
| 2004/0010215 A1 | 1/2004 | Gibbins et al. |
| 2004/0082925 A1 | 4/2004 | Patel |
| 2004/0096410 A1 | 5/2004 | Maley et al. |
| 2004/0108462 A1 | 6/2004 | Besesty et al. |
| 2004/0127025 A1 | 7/2004 | Crocker et al. |
| 2004/0147618 A1 | 7/2004 | Lee et al. |

(56) References Cited

U.S. PATENT DOCUMENTS

| | | |
|---|---|---|
| 2004/0170545 A1 | 9/2004 | Emanuel |
| 2004/0173056 A1 | 9/2004 | McNally et al. |
| 2004/0180093 A1 | 9/2004 | Burton et al. |
| 2004/0253536 A1 | 12/2004 | Park et al. |
| 2004/0254532 A1 | 12/2004 | Mehier |
| 2005/0008861 A1 | 1/2005 | Yadav et al. |
| 2005/0029121 A1 | 2/2005 | Monzyk et al. |
| 2005/0186135 A1 | 8/2005 | Howes |
| 2005/0265894 A1 | 12/2005 | Monzyk et al. |
| 2006/0276740 A1 | 12/2006 | Bagley |
| 2007/0003603 A1 | 1/2007 | Karandikar et al. |
| 2007/0207335 A1 | 9/2007 | Karandikar et al. |
| 2007/0254044 A1 | 11/2007 | Karandikar et al. |
| 2007/0293800 A1 | 12/2007 | McMaken et al. |
| 2009/0035342 A1 | 2/2009 | Karandikar et al. |
| 2010/0034882 A1 | 2/2010 | Gibbins et al. |

FOREIGN PATENT DOCUMENTS

| | | |
|---|---|---|
| EP | 0072251 A2 | 2/1983 |
| EP | 0297769 A1 | 1/1989 |
| EP | 0489206 A1 | 6/1992 |
| EP | 0 500 387 A2 | 8/1992 |
| EP | 0707793 A | 4/1996 |
| EP | 0709101 A2 | 5/1996 |
| EP | 1245239 A1 | 10/2002 |
| EP | 1388561 A2 | 2/2004 |
| GB | 863875 A | 3/1961 |
| GB | 1471013 A | 4/1977 |
| GB | 1554002 A | 10/1979 |
| GB | 2 024 012 A | 1/1980 |
| GB | 2134791 A | 8/1984 |
| JP | 1 544 002 | 10/1979 |
| JP | 06-145060 A | 5/1994 |
| JP | 6248549 A | 9/1994 |
| JP | 7097767 A | 4/1995 |
| JP | 11302119 A | 11/1999 |
| JP | 2003529630 A | 10/2003 |
| JP | 2004137615 A | 5/2004 |
| JP | 2004161632 A | 6/2004 |
| WO | WO-84/01721 A1 | 5/1984 |
| WO | WO-88/06894 A1 | 9/1988 |
| WO | WO-90/03810 A1 | 4/1990 |
| WO | WO-96/11572 A1 | 4/1996 |
| WO | WO-98/06260 A1 | 2/1998 |
| WO | WO-98/20719 A1 | 5/1998 |
| WO | WO-99/15101 A2 | 4/1999 |
| WO | WO-99/25395 A2 | 5/1999 |
| WO | WO-00/09173 A1 | 2/2000 |
| WO | WO-00/15202 A2 | 3/2000 |
| WO | WO-01/11955 A2 | 2/2001 |
| WO | WO-01/24839 A1 | 4/2001 |
| WO | WO-01/49258 A2 | 7/2001 |
| WO | WO-0226039 A1 | 4/2002 |
| WO | WO-0243743 A1 | 6/2002 |
| WO | WO-02/061403 A1 | 8/2002 |
| WO | WO-02/076518 A1 | 10/2002 |
| WO | WO-03/002089 A1 | 1/2003 |
| WO | WO-03/080231 A1 | 10/2003 |
| WO | WO-04/001880 A1 | 12/2003 |
| WO | WO-2004/010952 A2 | 2/2004 |
| WO | WO-2004/028255 A1 | 4/2004 |
| WO | WO-2004/056404 A2 | 7/2004 |
| WO | WO-2006/015317 A2 | 2/2006 |
| WO | WO-2006/026026 A2 | 3/2006 |
| WO | WO-2006/034249 A2 | 3/2006 |
| WO | WO-2007/095058 A2 | 8/2007 |
| WO | WO-2007/127236 A2 | 11/2007 |
| WO | WO-2008/131070 A1 | 10/2008 |

OTHER PUBLICATIONS

Acticoat RTM, Silver Coated Dressing Marketing Materials. The Westaim Corporation, 1988.

Bharathi, Subramanian et al., "Sol-Gel-Derived Nanocrystalline Gold—Silicate Composite Biosensor," Analytical Communications, 1998, 35: 29-31.

Chase, Grafton D., Pharmaceutical Science by Remington, 14th Edition., Mack Publishing Co., Rheology, Newtonian Flow-Plastic Flow-Pseudoplastic Flow-Dilatant Flow-Methods for Measuring Viscosity-Polymer Solutions-Thixotrophy-Pharmaceutical Applications, 1970, 359-371.

ConvaTec Corp. Aquacel Ag Product Info from website. [internet citation] Retrieved Dec. 9, 2002 from http://www.convatec.com/en_US/company/pr/index.html.

Cooper, Rose, "A Review of the Evidence for the Use of Topical Antimicrobial Agents in Wound Care," World Wide Wounds, 2004, 1-15.

Deitch, E. et al., "Silver-Nylon: a New Antimicrobial Agent". Antimicrobial Agents and Chemotherapy, 1983, 23(3):356-359.

Deitch, E., et al., Abstract, "Silver-impregnated nylon cloth dressing: in vitro and in vivo evaluation of antimicrobial activity," J. Trauma, 1987, pp. 301-304, vol. 27, No. 3.

FDA Approval Letter to begin OxyGenesis marketing. Sep. 19, 2008.

Feng et al, "Study of the initiation mechanism of the vinyl polymerization with the system persulfate/N,N,N',N'-tetramethylethylenediamine," Makromol. Chem. 1988, 189: 77-83.

Fox, Jr., Charles L., "Silver Sulfadiazine—A New Topical", Arch. Surg., vol. 96, pp. 184-188, 1968.

Gibbins et al., AcryDerm Absorbent Oxygen Dressing Point of Use Evaluation: Summary of Results. Draft. Jul. 17, 2009.

Gibbins, B. and Hopman, L., "A Comparison of a New Anti-Microbial Polyacrylate Absorbent Wound Dressing Containing Silver with the Silver-containing Anti-microbial Film Dressings", Presentation at Clinical Symposium on Wound Care, Oct. 2, 1999.

Gibbins, Bruce, "The Antimicrobial Benefits of Silver and the Relevance of Microlattice Technology," Ostomy Wound Manage. Feb. 2003; Suppl:4-7.

Grier, N., "Silver and Its Compounds," Disinfection, Sterilization, and Preservation, 3rd Edition. Seymour S. Block, ed., Lea & Febiger, Philadelphia, 1983; Chapter 18, pp. 375-389.

Hackh's Chemical Dictionary, 4th Edition, McGraw Hill Book Co., New York, 1969; p. 451.

Handbook of Common Polymers, "Polyvinyl Alcohol Including Insolubilised Fibres," Scott & Roff, Jr., W.J., The Chemical Company, 1971, pp. 72-197.

Jia et al., "Effect of locally released oxygen on wound healing," Presented at 18th Annual Meeting of the Wound Healing Society, San Diego, CA. Apr. 2008.

Junhui He et al, "Facile in situ synthesis of noble metal nanoparticles in porous cellulose fibers," Chemistry of Materials, 2003, 15(23): 4401-4406.

Kapoor, Sudhir, "Preparation, Characterization, and Surface Modification of Silver Particles," Langmuir, 1998, 14 (5):1021-1025.

MacKeen, P., et al., "Silver-Coated Nylon Fiber as an Antibacterial Agent," Antimicrobial Agents and Chemotherapy, 1987, 31(1): 93-99.

Silver, Simon, "Bacterial Silver Resistance: Molecular Biology and Uses and Misuses of Silver Compounds," FEMS Microbiology Reviews, 2003, pp. 341-353.

Topical Delivery Methods, undated reference, retrieved from file on May 11, 2011.

Wang et al., "Directing oleate stabilized nanosized silver colloids into organic phases", Langmuir: The ACS Journal of Surfaces and Colloids. 1998; 14:602-610.

Communication regarding the expiration of oppposition period issued on Feb. 10, 2006 for European Pat. App. No. 98961733.7 which claims priority to PCT/US98/024272 filed on Nov. 13, 1998, published May 27, 1999 as WO 99/027680 (Applicant—Acrymed; Inventors: B.L. Gibbins).

Decision to grant a European Pat. issued on Feb. 24, 2005 for European Pat. App. No. 98961733.7 which claims priority to PCT/US98/024272 filed on Nov. 13, 1998, published May 27, 1999 as WO 99/027680 (Applicant—Acrymed; Inventors: B.L. Gibbins).

Approval of request for amendments/corrections issued on Feb. 15, 2005 for European Pat. App. No. 98961733.7 which claims priority to

(56) References Cited

OTHER PUBLICATIONS

PCT/US98/024272 filed on Nov. 13, 1998, published 05-27-1999 as WO 99/027680 (Applicant—Acrymed; Inventors: B.L. Gibbins).
Reply to communication from the Examining Division filed on Dec. 22, 2004 for European Pat. App. No. 98961733.7 which claims priority to PCT/US98/024272 filed on Nov. 13, 1998, published May 27, 1999 as WO 99/027680 (Applicant—Acrymed; Inventors: B.L. Gibbins).
Result of Consultation by telephone/in person (with time limit) issued on Nov. 9, 2004 for European Pat. App. No. 98961733.7 which claims priority to PCT/US98/024272 filed on Nov. 13, 1998, published May 27, 1999 as WO 99/027680 (Applicant—Acrymed; Inventors: B.L. Gibbins).
Request for correction amendment of the text proposed for grant filed on Oct. 26, 2004 for European Pat. App. No. 98961733.7 which claims priority to PCT/US98/024272 filed on Nov. 13, 1998, published May 27, 1999 as WO 99/027680 (Applicant—Acrymed; Inventors: B.L. Gibbins).
Communication about intention to grant a European Pat. issued on Jun. 18, 2004 for European Pat. App. No. 98961733.7 which claims priority to PCT/US98/024272 filed on Nov. 13, 1998, published May 27, 1999 as WO 99/027680 (Applicant—Acrymed; Inventors. B.L. Gibbins).
Reply to communication from the Examining Division filed on Aug. 20, 2003 for European Pat. App. No. 98961733.7 which claims priority to PCT/US98/024272 filed on Nov. 13, 1998, published May 27, 1999 as WO 99/027680 (Applicant—Acrymed; Inventors: B.L. Gibbins).
Communication from the Examining Division issued on May 5, 2003 for European Pat. App. No. 98961733.7 which claims priority to PCT/US98/024272 filed on Nov. 13, 1998, published May 27, 1999 as WO 99/027680 (Applicant—Acrymed; Inventors: B.L. Gibbins).
Reply to communication from the Examining Division filed on Feb. 5, 2003 for European Pat. App. No. 98961733.7 which claims priority to PCT/US98/024272 filed on Nov. 13, 1998, published May 27, 1999 as WO 99/027680 (Applicant—Acrymed; Inventors: B.L. Gibbins).
Communication from the Examining Division issued on Aug. 1, 2002 for European Pat. App. No. 98961733.7 which claims priority to PCT/US98/024272 filed on Nov. 13, 1998, published May 27, 1999 as WO 99/027680 (Applicant—Acrymed; Inventors: B.L. Gibbins).
Reply to communication from the Examining Division filed on May 20, 2002 for European Pat. App. No. 98961733.7 which claims priority to PCT/US98/024272 filed on Nov. 13, 1998, published May 27, 1999 as WO 99/027680 (Applicant—Acrymed; Inventors: B.L. Gibbins).
Communication from the Examining Division issued Jul. 31, 2001 for European Pat. App. No. 98961733.7 which claims priority to PCT/US98/024272 filed on Nov. 13, 1998, published May 27, 1999 as WO 99/027680 (Applicant—Acrymed; Inventors: B.L. Gibbins).
PCT Intl. Search Report issued on Jun. 23, 1999 for PCT/US98/24272, filed on Nov. 13, 1998, published May 27, 1999 as WO 99/027680 (Applicant—Acrymed; Inventors: B.L. Gibbins).
PCT Intl. Preliminary exam report issued on Aug. 8, 2001 for PCT/US98/24272, filed on Nov. 13, 1998, published May 27, 1999 as WO 99/027680 (Applicant—Acrymed; Inventors: B.L. Gibbins).
PCT Written opinion issued on Feb. 18, 2000 for PCT/US98/24272, filed on Nov. 13, 1998, published May 27, 1999 as WO 99/027680 (Applicant—Acrymed; Inventors: B.L. Gibbins).
Issue Notification issued on Jul. 14, 1999 for U.S. Appl. No. 08/971,074, filed Nov. 14, 1997 (Inventor—B.L. Gibbins).
Notice of Allowance issued on Feb. 25, 1999 for U.S. Appl. No. 08/971,074, filed Nov. 14, 1997 (Inventor—B.L. Gibbins).
Examiner Interview Summary/Amendment issued on Dec. 11, 1998 for U.S. Appl. No. 08/971,074, filed Nov. 14, 1997 (Inventor—B.L. Gibbins).
Response after Non-Final Action filed on Nov. 18, 1998 for U.S. Appl. No. 08/971,074, filed Nov. 14, 1997 (Inventor—B.L. Gibbins).
Non-Final Rejection issued on Aug. 19, 1998 for U.S. Appl. No. 08/971,074, filed Nov. 14, 1997 (Inventor—B.L. Gibbins).
Response to Election / Restriction filed on Jul. 14, 1998 for U.S. Appl. No. 08/971,074, filed Nov. 14, 1997 (Inventor —B.L. Gibbins).
Restriction Requirement issued on May 21, 1998 for U.S. Appl. No. 08/971,074, filed Nov. 14, 1997 (Inventor—B.L. Gibbins).
Issue Notification issued on Mar. 12, 2002 for U.S. Appl. No. 09/191,223, filed Nov. 13, 1998 (Inventor—B.L. Gibbins).
Notice of Allowance issued on Sep. 25, 2001 for U.S. Appl. No. 09/191,223, filed Nov. 13, 1998 (Inventor—B.L. Gibbins).
Notice of Allowance issued on Oct. 3, 2000 for U.S. Appl. No. 09/191,223, filed Nov. 13, 1998 (Inventor—B.L. Gibbins).
Response after Non-Final Action filed on Aug. 11, 2000 for U.S. Appl. No. 09/191,223, filed Nov. 13, 1998 (Inventor—B.L. Gibbins).
Non-Final Rejection issued on Apr. 11, 2000 for U.S. Appl. No. 09/191,223, filed Nov. 13, 1998 (Inventor—B.L. Gibbins).
Response to Election / Restriction filed on Mar. 21, 2000 for U.S. Appl. No. 09/191,223, filed Nov. 13, 1998 (Inventor—B.L. Gibbins).
Restriction Requirement issued on Feb. 22, 2000 for U.S. Appl. No. 09/191,223, filed Nov. 13, 1998 (Inventor—B.L. Gibbins).
Communication regarding the expiry of opposition period issued on Sep. 2, 2009 for EP App. No. 970522.9, which claims priority to Intl. Pat. App. No. PCT/US00/26890, filed Sep. 29, 200, published on Apr. 12, 2001 as WO 01/024839 (Applicant—Acrymed, Inc.).
Decision to grant a European Pat. issued on Oct. 2, 2008 for EP App. No. 970522.9, which claims priority to Intl. Pat. App. No. PCT/US00/26890, filed Sep. 29, 200, published on Apr. 12, 2001 as WO 01/024839 (Applicant—Acrymed, Inc.).
Communication about intention to grant a European Pat. issued on Apr. 10, 2008 for EP App. No. 970522.9, which claims priority to Intl. Pat. App. No. PCT/US00/26890, filed Sep. 29, 200, published on Apr. 12, 2001 as WO 01/024839 (Applicant—Acrymed, Inc.).
Reply to communication from the Examining Division filed on Feb. 26, 2008 for EP App. No. 970522.9, which claims priority to Intl. Pat. App. No. PCT/US00/26890, filed Sep. 29, 200, published on Apr. 12, 2001 as WO 01/024839 (Applicant—Acrymed, Inc.).
Communication from the Examining Division issued on Oct. 18, 2007 for EP App. No. 970522.9, which claims priority to Intl. Pat. App. No. PCT/US00/26890, filed Sep. 29, 200, published on Apr. 12, 2001 as WO 01/024839 (Applicant—Acrymed, Inc.).
Reply to communication from the Examining Division filed on Dec. 28, 2006 for EP App. No. 970522.9, which claims priority to Intl. Pat. App. No. PCT/US00/26890, filed Sep. 29, 200, published on Apr. 12, 2001 as WO 01/024839 (Applicant—Acrymed, Inc.).
Communication from the Examining Division issued on Sep. 1, 2006 for EP App. No. 970522.9, which claims priority to Intl. Pat. App. No. PCT/US00/26890, filed Sep. 29, 200, published on Apr. 12, 2001 as WO 01/024839 (Applicant—Acrymed, Inc.).
Reply to communication from the Examining Division filed on Mar. 21, 2005 for EP App. No. 970522.9, which claims priority to Intl. Pat. App. No. PCT/US00/26890, filed Sep. 29, 200, published on Apr. 12, 2001 as WO 01/024839 (Applicant—Acrymed, Inc.).
Communication from the Examining Division issued on Sep. 20, 2004 for EP App. No. 970522.9, which claims priority to Intl. Pat. App. No. PCT/US00/26890, filed Sep. 29, 200, published on Apr. 12, 2001 as WO 01/024839 (Applicant—Acrymed, Inc.).
Reply to communication from the Examining Division filed on Feb. 27, 2003 for EP App. No. 970522.9, which claims priority to Intl. Pat. App. No. PCT/US00/26890, filed Sep. 29, 200, published on Apr. 12, 2001 as WO 01/024839 (Applicant—Acrymed, Inc.).
Communication from the Examining Division issued on Aug. 21, 2003 for EP App. No. 970522.9, which claims priority to Intl. Pat. App. No. PCT/US00/26890, filed Sep. 29, 200, published on Apr. 12, 2001 as WO 01/024839 (Applicant—Acrymed, Inc.).
PCT Intl. Search Report issued on Feb. 5, 2001 for PCT/US00/26890, filed on Sep. 29, 2000, published Apr. 12, 2001 as WO 01/24839 (Applicant—Acrymed; Inventors: Gibbins).
PCT Written Opinion issued on Jul. 23, 2001 for PCT/US00/26890, filed on Sep. 29, 2000, published Apr. 12, 2001 as WO 01/24839 (Applicant—Acrymed; Inventors: Gibbins).
PCT Intl. Preliminary Examination Report issued on Oct. 17, 2001 for PCT/US00/26890, filed on Sep. 29, 2000, published Apr. 12, 2001 as WO 01/24839 (Applicant—Acrymed; Inventors: Gibbins).
Notice of Allowance issued on Apr. 15, 2003 for U.S. Appl. No. 09/675,892, filed Sep. 29, 2000 (Inventor—B.L. Gibbins).

(56) References Cited

OTHER PUBLICATIONS

Amendment/Response After Non-Final Rejection filed on Mar. 21, 2003 for U.S. Appl. No. 09/675,892, filed Sep. 29, 2000 (Inventor—B.L. Gibbins).

Non-Final Rejection issued on Nov. 21, 2002 for U.S. Appl. No. 09/675,892, filed Sep. 29, 2000 (Inventor—B.L. Gibbins).

Amendment After Final filed on Oct. 30, 2002 for U.S. Appl. No. 09/675,892, filed Sep. 29, 2000 (Inventor—B.L. Gibbins).

Final Rejection issued on Jul. 31, 2002 for U.S. Appl. No. 09/675,892, filed Sep. 29, 2000 (Inventor—B.L. Gibbins).

Amendment/Response After Non-Final Rejection filed on Apr. 18, 2002 for U.S. Appl. No. 09/675,892, filed Sep. 29, 2000 (Inventor—B.L. Gibbins).

Non-Final Rejection issued on Jan. 18, 2002 for U.S. Appl. No. 09/675,892, filed Sep. 29, 2000 (Inventor—B.L. Gibbins).

Notice of Allowance issued on Mar. 7, 2005 for U.S. Appl. No. 10/441,275, filed May 19, 2003 (Inventor—B.L. Gibbins).

Notice of Allowance/Examiner Interview Summary Record issued on Jul. 2, 2004 for U.S. Appl. No. 10/441,275, filed May 19, 2003 (Inventor—B.L. Gibbins).

Examiner Interview Summary Record (PTOL-413) issued May 26, 2004 for U.S. Appl. No. 10/441,275, filed May 19, 2003 (Inventor—B.L. Gibbins).

Supplemental Preliminary Amendment filed on Mar. 25, 2004 for U.S. Appl. No. 10/441,275, filed May 19, 2003 (Inventor—B.L. Gibbins).

Preliminary Amendment filed on Dec. 2, 2003 for U.S. Appl. No. 10/441,275, filed May 19, 2003 (Inventor—B.L. Gibbins).

Issue Notification issued on Jul. 29, 2009 for U.S. Appl. No. 10/978,556, filed Nov. 1, 2004 (Inventor—B.L. Gibbins).

Notice of Allowance issued on Apr. 16, 2009 for U.S. Appl. No. 10/978,556, filed Nov. 1, 2004 (Inventor—B.L. Gibbins).

Terminal Disclaimer/Amendment After Final Rejection filed on Apr. 6, 2009 for U.S. Appl. No. 10/978,556, filed Nov. 1, 2004 (Inventor—B.L. Gibbins).

Final Rejection issued on Nov. 6, 2008 for U.S. Appl. No. 10/978,556, filed Nov. 1, 2004 (Inventor—B.L. Gibbins).

Amendment/Response After Non-Final Rejection filed on Aug. 1, 2008 for U.S. Appl. No. 10/978,556, filed Nov. 1, 2004 (Inventor—B.L. Gibbins).

Non-Final Rejection issued on Apr. 1, 2008 for U.S. Appl. No. 10/978,556, filed Nov. 1, 2004 (Inventor—B.L. Gibbins).

Amendment Submitted/Entered with CPA/RCE filed on Oct. 31, 2007 for U.S. Appl. No. 10/978,556, filed Nov. 1, 2004 (Inventor—B.L. Gibbins).

Advisory Action (PTOL-303) issued on Oct. 3, 2007 for U.S. Appl. No. 10/978,556, filed Nov. 1, 2004 (Inventor—B.L. Gibbins).

Amendment After Final Rejection filed on Sep. 13, 2007 for U.S. Appl. No. 10/978,556, filed Nov. 1, 2004 (Inventor—B.L. Gibbins).

Final Rejection issued on Jul. 13, 2007 for U.S. Appl. No. 10/978,556, filed Nov. 1, 2004 (Inventor—B.L. Gibbins).

Amendment/Response After Non-Final Rejection filed on Apr. 24, 2007 for U.S. Appl. No. 10/978,556, filed Nov. 1, 2004 (Inventor—B.L. Gibbins).

Non-Final Rejection issued on Jan. 24, 2007 for U.S. Appl. No. 10/978,556, filed Nov. 1, 2004 (Inventor—B.L. Gibbins).

Response to Election / Restriction filed on Nov. 13, 2006 for U.S. Appl. No. 10/978,556, filed Nov. 1, 2004 (Inventor—B.L. Gibbins).

Requirement for Restriction/Election issued on Oct. 11, 2006 for U.S. Appl. No. 10/978,556, filed Nov. 1, 2004 (Inventor—B.L. Gibbins).

Preliminary Amendment filed on Feb. 15, 2005 for U.S. Appl. No. 10/978,556, filed Nov. 1, 2004 (Inventor—B.L. Gibbins).

Reexamination Certificate Issued on Jun. 16, 2009 for Inter Partes Reexam No. 95/000,042 of U.S. Pat. 6,605,751 granted Aug. 12, 2003 (Gibbins et al.).

Notice of Intent to Issue a Reexam Certificate issued on Mar. 25, 2009 for Inter Partes Reexam No. 95/000,042 of U.S. Pat. 6,605,751 granted Aug. 12, 2003 (Gibbins et al.).

Right of Appeal Notice issued on Dec. 9, 2008 for Inter Partes Reexam No. 95/000,042 of U.S. Pat. 6,605,751 granted Aug. 12, 2003 (Gibbins et al.).

Action Closing Prosecution (nonfinal) issued on Aug. 19, 2008 for Inter Partes Reexam No. 95/000,042 of U.S. Pat. 6,605,751 granted Aug. 12, 2003 (Gibbins et al.).

Response after non-final action-owner filed on Oct. 8, 2004 for Inter Partes Reexam No. 95/000,042 of U.S. Pat. 6,605,751 granted Aug. 12, 2003 (Gibbins et al.).

Reexam Ordered and Non-Final Action issued on Aug. 4, 2004 for Inter Partes Reexam No. 95/000,042 of U.S. Pat. 6,605,751 granted Aug. 12, 2003 (Gibbins et al.).

Ex Parte Reexam request filed on May 13, 2004 for Inter Partes Reexam No. 95/000,042 of U.S. Pat. 6,605,751 granted Aug. 12, 2003 (Gibbins et al.).

Notice of Allowance issued on May 12, 2011 for U.S. Appl. No. 12/510,651, filed Jul. 28, 2009 (Inventor—Gibbins).

Amendment/Response After Non-Final Reject/Terminal Disclaimer filed on Apr. 4, 2011 for U.S. Appl. No. 12/510,651, filed Jul. 28, 2009 (Inventor—Gibbins).

Non-Final Rejection issued on Jan. 5, 2011 for U.S. Appl. No. 12/510,651, filed Jul. 28, 2009 (Inventor—Gibbins).

Preliminary Amendment filed on Oct. 28, 2009 for U.S. Appl. No. 12/510,651, filed Jul. 28, 2009 (Inventor—Gibbins).

Communication regarding the expiry of opposition period issued on Apr. 4, 2007 for EP App. No. 990393.1, which claims priority to PCT/US00/35560, filed on Dec. 29, 2000, published Jul. 12, 2001 as WO 01/49258 (Applicant—Acrymed).

Decision to grant a European Pat. issued on Apr. 21, 2006 for EP App. No. 990393.1, which claims priority to PCT/US00/35560, filed on Dec. 29, 2000, published Jul. 12, 2001 as WO 01/49258 (Applicant—Acrymed).

Reply to communication about intention to grant filed on Mar. 28, 2006 for EP App. No. 990393.1, which claims priority to PCT/US00/35560, filed on Dec. 29, 2000, published Jul. 12, 2001 as WP 01/49258 (Applicant—Acrymed).

Communication about intention to grant a European Pat. filed on Nov. 28, 2005 for EP App. No. 990393.1, which claims priority to PCT/US00/35560, filed on Dec. 29, 2000, published Jul. 12, 2001 as WO 01/49258 (Applicant—Acrymed).

Reply to communication from the Examining Division filed on Aug. 30, 2005 for EP App. No. 990393.1, which claims priority to PCT/US00/35560, filed on Dec. 29, 2000, published Jul. 12, 2001 as WO 01/49258 (Applicant—Acrymed).

Communication from the Examining Division issued on Feb. 22, 2005 for EP App. No. 990393.1, which claims priority to PCT/US00/35560, filed on Dec. 29, 2000, published Jul. 12, 2001 as WO 01/49258 (Applicant—Acrymed).

Reply to communication from the Examining Division filed on Apr. 1, 2004 for EP App. No. 990393.1, which claims priority to PCT/US00/35560, filed on Dec. 29, 2000, published Jul. 12, 2001 as WO 01/49258 (Applicant—Acrymed).

Communication from the Examining Division issued on Feb. 13, 2004 for EP App. No. 990393.1, which claims priority to PCT/US00/35560, filed on Dec. 29, 2000, published Jul. 12, 2001 as WO 01/49258 (Applicant—Acrymed).

Reply to communication from the Examining Division filed on Jul. 24, 2003 for EP App. No. 990393.1, which claims priority to PCT/US00/35560, filed on Dec. 29, 2000, published Jul. 12, 2001 as WO 01/49258 (Applicant—Acrymed).

Communication from the Examining Division issued on Jan. 23, 2003 for EP App. No. 990393.1, which claims priority to PCT/US00/35560, filed on Dec. 29, 2000, published Jul. 12, 2001 as WO 01/49258 (Applicant—Acrymed).

Amendments before examination filed on Oct. 18, 2002 for EP App. No. 990393.1, which claims priority to PCT/US00/35560, filed on Dec. 29, 2000, published Jul. 12, 2001 as WO 01/49258 (Applicant—Acrymed).

Amendments before examination filed on Jul. 19, 2002 for EP App. No. 990393.1, which claims priority to PCT/US00/35560, filed on Dec. 29, 2000, published Jul. 12, 2001 as WO 01/49258 (Applicant—Acrymed).

(56) References Cited

OTHER PUBLICATIONS

PCT Intl. Search Report issued on Jul. 12, 2001 for PCT/US00/35560, filed on Dec. 29, 2000, published Jul. 12, 2001 as WO 01/49258 (Applicant—Acrymed; Inventors: Gibbins).
PCT Intl. Preliminary Examination Report issued on Apr. 2, 2002 for PCT/US00/35560, filed on Dec. 29, 2000, published Jul. 12, 2001 as WO 01/49258 (Applicant—Acrymed; Inventors: Gibbins).
Issue Notification issued on Dec. 20, 2006 for U.S. Appl. No. 10/441,141, filed May 19, 2003 (Inventor—Gibbins).
Notice of Allowance/Examiner Interview Summary Record (PTOL-413) issued on Jul. 25, 2006 for U.S. Appl. No. 10/441,141, filed May 19, 2003 (Inventor—Gibbins).
Amendment After Final Rejection filed on Jul. 5, 2006 for U.S. Appl. No. 10/441,141, filed May 19, 2003 (Inventor—Gibbins).
Examiner Interview Summary Record (PTOL-413) issued on Jun. 28, 2006 for U.S. Appl. No. 10/441,141, filed May 19, 2003 (Inventor—Gibbins).
Final Rejection issued on May 4, 2006 for U.S. Appl. No. 10/441,141, filed May 19, 2003 (Inventor—Gibbins).
Amendment/Response After Non-Final Action filed on Feb. 14, 2006 for U.S. Appl. No. 10/441,141, filed May 19, 2003 (Inventor—Gibbins).
Non-Final Rejection issued on Nov. 15, 2005 for U.S. Appl. No. 10/441,141, filed May 19, 2003 (Inventor—Gibbins).
Preliminary Amendment filed on Apr. 12, 2003 for U.S. Appl. No. 10/441,141, filed May 19, 2003 (Inventor—Gibbins).
Notification of Grant issued Feb. 5, 2010 for Chinese Pat. App. No. 03820077.5, which claims priority to PCT/US03/023851 filed Jul. 29, 2003, published Feb. 5, 2004 as WO 04/010952 (Applicant—Acrymed, Inc.).
Response to fifth Office Action filed on Jan. 7, 2010 for Chinese Pat. App. No. 03820077.5, which claims priority to PCT/US03/023851 filed Jul. 29, 2003, published Feb. 5, 2004 as WO 04/010952 (Applicant—Acrymed, Inc.) + claims in English.
Fifth Office Action issued on Oct. 23, 2009 for Chinese Pat. App. No. 03820077.5, which claims priority to PCT/US03/023851 filed Jul. 29, 2003, published Feb. 5, 2004 as WO 04/010952 (Applicant—Acrymed, Inc.).
Response to fourth Office Action filed on Sep. 11, 2009 for Chinese Pat. App. No. 03820077.5, which claims priority to PCT/US03/023851 filed Jul. 29, 2003, published Feb. 5, 2004 as WO 04/010952 (Applicant—Acrymed, Inc.)—English translation only.
Fourth Office Action issued on Apr. 17, 2009 for Chinese Pat. App. No. 03820077.5, which claims priority to PCT/US03/023851 filed Jul. 29, 2003, published Feb. 5, 2004 as WO 04/010952 (Applicant—Acrymed, Inc.).
Response to third Office Action filed on Aug. 27, 2008 for Chinese Pat. App. No. 03820077.5, which claims priority to PCT/US03/023851 filed Jul. 29, 2003, published Feb. 5, 2004 as WO 04/010952 (Applicant—Acrymed, Inc.) claims in English.
Third Office Action issued on Jun. 13, 2008 for Chinese Pat. App. No. 03820077.5, which claims priority to PCT/US03/023851 filed Jul. 29, 2003, published Feb. 5, 2004 as WO 04/010952 (Applicant—Acrymed, Inc.).
Response to Second Office Action filed on Dec. 25, 2007 for Chinese Pat. App. No. 03820077.5, which claims priority to PCT/US03/023851 filed Jul. 29, 2003, published Feb. 5, 2004 as WO 04/010952 (Applicant—Acrymed, Inc.)—no translation available.
Second Office Action issed for Aug. 10, 2007 for Chinese Pat. App. No. 03820077.5, which claims priority to PCT/US03/023851 filed Jul. 29, 2003, published Feb. 5, 2004 as WO 04/010952 (Applicant—Acrymed, Inc.).
Response to first Office Action filed on Sep. 1, 2006 for Chinese Pat. App. No. 03820077.5, which claims priority to PCT/US03/023851 filed Jul. 29, 2003, published Feb. 5, 2004 as WO 04/010952 (Applicant—Acrymed, Inc.)—no translation available.
First Office Action issued on Apr. 21, 2006 for Chinese Pat. App. No. 03820077.5, which claims priority to PCT/US03/023851 filed Jul. 29, 2003, published Feb. 5, 2004 as WO 04/010952 (Applicant—Acrymed, Inc.).

Decision to Grant pursuant to Article 97(2) EPC issued on Dec. 2, 2010 for EP App. No. 3772113.1, which claims priority to PCT/US03/023851 filed Jul. 29, 2003, published Feb. 5, 2004 as WO 04/010952 (Applicant—Acrymed, Inc.).
Communication under Rule 71(3) EPC issued on Jun. 4, 2010 for EP App. No. 3772113.1, which claims priority to PCT/US03/023851 filed Jul. 29, 2003, published Feb. 5, 2004 as WO 04/010952 (Applicant—Acrymed, Inc.).
Letter during examination procedure after communication from the Examining Division filed on Jan. 19, 2010 for EP App. No. 3772113.1, which claims priority to PCT/US03/023851 filed Jul. 29, 2003, published Feb. 5, 2004 as WO 04/010952 (Applicant—Acrymed, Inc.).
Reply to communication from the Examining Division filed on Jan. 13, 2010 for EP App. No. 3772113.1, which claims priority to PCT/US03/023851 filed Jul. 29, 2003, published Feb. 5, 2004 as WO 04/010952 (Applicant—Acrymed, Inc.).
Communication from the Examining Division issued on Jul. 3, 2009 for EP App. No. 3772113.1, which claims priority to PCT/US03/023851 filed Jul. 29, 2003, published Feb. 5, 2004 as WO 04/010952 (Applicant—Acrymed, Inc.).
Reply to communication from the Examining Division filed on Jul. 15, 2008 for EP App. No. 3772113.1, which claims priority to PCT/US03/023851 filed Jul. 29, 2003, published Feb. 5, 2004 as WO 04/010952 (Applicant—Acrymed, Inc.).
Communication from the Examining Division issued on Jan. 10, 2008 for EP App. No. 3772113.1, which claims priority to PCT/US03/023851 filed Jul. 29, 2003, published Feb. 5, 2004 as WO 04/010952 (Applicant—Acrymed, Inc.).
Supplementary European search report issued on Dec. 14, 2006 for EP App. No. 3772113.1, which claims priority to PCT/US03/023851 filed Jul. 29, 2003, published Feb. 5, 2004 as WO 04/010952 (Applicant—Acrymed, Inc.).
Preliminary Amendment filed on Apr. 12, 2005 for EP App. No. 3772113.1, which claims priority to PCT/US03/023851 filed Jul. 29, 2003, published Feb. 5, 2004 as WO 04/010952 (Applicant—Acrymed, Inc.).
PCT Intl. Search Report issued on Aug. 27, 2004 for Intl. App. No. PCT/US03/023851 filed Jul. 29, 2003, published Feb. 5, 2004 as WO 04/010952 (Applicant—AcryMed, Inc.).
Issue Notification issued on Jul. 6, 2005 for U.S. Appl. No. 10/207,936, filed Jul. 29, 2002 (Inventor—Maley, J. C.).
Amendment/Response-After Non-Final Rejection filed on Apr. 25, 2005 for U.S. Appl. No. 10/207,936, filed Jul. 29, 2002 (Inventor—Maley, J. C.).
Office Communication issued on Mar. 30, 2005 for U.S. Appl. No. 10/207,936, filed Jul. 29, 2002 (Inventor—Maley, J. C.).
Notice of Allowance and Fees Due (PTOL-85) with Examiner Interview Summary Record (PTOL-413) issued Feb. 16, 2005 for U.S. Appl. No. 10/207,936, filed Jul. 29, 2002 (Inventor—Maley, J. C.).
Supplemental Amendment after Final Rejection issed on Jan. 28, 2005 for U.S. Appl. No. 10/207,936, filed Jul. 29, 2002 (Inventor—Maley, J. C.).
Response After Final Rejection filed on Jan. 12, 2005 for U.S. Appl. No. 10/207,936, filed Jul. 29, 2002 (Inventor—Maley, J. C.).
Final Rejection issued on Nov. 23, 2004 for U.S. Appl. No. 10/207,936, filed Jul. 29, 2002 (Inventor—Maley, J. C.).
Response After Non-Final Rejection filed on Jul. 29, 2004 for U.S. Appl. No. 10/207,936, filed Jul. 29, 2002 (Inventor—Maley, J. C.).
Non-Final Rejection issued on Apr. 29, 2004 for U.S. Appl. No. 10/207,936, filed Jul. 29, 2002 (Inventor—Maley, J. C.).
Response After Non-Final Rejection filed on Jan. 22, 2004 for U.S. Appl. No. 10/207,936, filed Jul. 29, 2002 (Inventor—Maley, J. C.).
Non-Final Rejection issued on Oct. 22, 2003 for U.S. Appl. No. 10/207,936, filed Jul. 29, 2002 (Inventor—Maley, J. C.).
Non-Final Rejection issued on Jun. 28, 2011 for U.S. Appl. No. 10/630,627, filed Jul. 29, 2003 (Inventor—Maley, J.C.).
Response After Non-Compliant Amendment filed on Jun. 2, 2010 for U.S. Appl. No. 10/630,627, filed Jul. 29, 2003 (Inventor—Maley, J.C.).
Amendment Submitted/Entered with CPA/RCE filed on Apr. 27, 2010 for U.S. Appl. No. 10/630,627, filed Jul. 29, 2003 (Inventor—Maley, J.C.).

(56) References Cited

OTHER PUBLICATIONS

Final Rejection issued on Dec. 3, 2009 for U.S. Appl. No. 10/630,627, filed Jul. 29, 2003 (Inventor—Maley, J.C.).
Response After Non-Final Rejection filed on Jul. 20, 2009 for U.S. Appl. No. 10/630,627, filed Jul. 29, 2003 (Inventor—Maley, J.C.).
Non-Final Rejection issued on Feb. 19, 2009 for U.S. Appl. No. 10/630,627, filed Jul. 29, 2003 (Inventor—Maley, J.C.).
Amendment Submitted/Entered with CPA/RCE filed on Nov. 26, 2008 for U.S. Appl. No. 10/630,627, filed Jul. 29, 2003 (Inventor—Maley, J.C.).
Final Rejection issued on Jun. 26, 2008 for U.S. Appl. No. 10/630,627, filed Jul. 29, 2003 (Inventor—Maley, J.C.).
Response After Non-Final Rejection filed on Feb. 7, 2008 for U.S. Appl. No. 10/630,627, filed Jul. 29, 2003 (Inventor —Maley, J.C.).
Non-Final Rejection issued on Sep. 7, 2007 for U.S. Appl. No. 10/630,627, filed Jul. 29, 2003 (Inventor—Maley, J.C.).
Amendment Submitted/Entered with CPA/RCE filed on Jun. 22, 2007 for U.S. Appl. No. 10/630,627, filed Jul. 29, 2003 (Inventor—Maley, J.C.).
Advisory Action (PTOL-303) issued on May 17, 2007 for U.S. Appl. No. 10/630,627, filed Jul. 29, 2003 (Inventor—Maley, J.C.).
Amendment After Final Rejection filed on Apr. 23, 2007 for U.S. Appl. No. 10/630,627, filed Jul. 29, 2003 (Inventor—Maley, J.C.).
Final Rejection issued on Feb. 23, 2007 for U.S. Appl. No. 10/630,627, filed Jul. 29, 2003 (Inventor—Maley, J.C.).
Response After Non-Final Rejection filed on Nov. 21, 2006 for U.S. Appl. No. 10/630,627, filed Jul. 29, 2003 (Inventor—Maley, J.C.).
Non-Final Rejection issued on Aug. 24, 2006 for U.S. Appl. No. 10/630,627, filed Jul. 29, 2003 (Inventor—Maley, J.C.).
Response to Election / Restriction Filed on Jun. 23, 2006 for U.S. Appl. No. 10/630,627, filed Jul. 29, 2003 (Inventor —Maley, J.C.).
Restriction/Election Requirement issued on May 23, 2006 for U.S. Appl. No. 10/630,627, filed Jul. 29, 2003 (Inventor—Maley, J.C.).
Response to First Office Action filed on Jul. 9, 2009 for Chinese Pat. App. No. 200580028750.9, which claims priority to Intl. App. No. PCT/US/05/027260 filed Aug. 1, 2005, published Feb. 9, 2006 as WO 06/015317 (Applicant—Acrymed, Inc.)—Proposed Claims in English.
First Office Action issued on Dec. 26, 2008 for Chinese Pat. App. No. 200580028750.9, which claims priority to Intl. App. No. PCT/US/05/027260 filed Aug. 1, 2005, published Feb. 9, 2006 as WO 06/015317 (Applicant—Acrymed, Inc.).
Amended claims filed on Feb. 26, 2007 for EP App. No. 05778379.7, which claims priority to Intl. App. No. PCT/US05/027260 filed Aug. 1, 2005, published Feb. 9, 2006 as WO 06/015317 (Applicant—Acrymed, Inc.).
Response to Examiner's Report filed on Jun. 29, 2011 for Indian Pat. App 735/KOLNP/2007, which claims priority to Intl. Pat. App. No. PCT/US05/027260, filed on Aug. 1, 2005, published on Mar. 9, 2006 as WO 06/015317 (Applicant—Acrymed, Inc.).
Examiner's Report issued on Jun. 29, 2010 for Indian Pat. App 735/KOLNP/2007, which claims priority to Intl. Pat. App. No. PCT/US05/027260, filed on Aug. 1, 2005, published on Mar. 9, 2006 as WO 06/015317 (Applicant—Acrymed, Inc.).
Intl. Preliminary Report on Patentability issued on Jan. 30, 2007 for Intl. App. No. PCT/US05/027260 filed Aug. 1, 2005, published Feb. 9, 2006 as WO 06/015317 (Applicant—Acrymed, Inc.).
Intl. Search Report with Written Opinion issued on Apr. 28, 2006 for Intl. App. No. PCT/US05/027260 filed Aug. 1, 2005, published Feb. 9, 2006 as WO 06/015317 (Applicant—Acrymed, Inc.).
Response to Restriction Requirement filed on Aug. 9, 2011 for U.S. Appl. No. 11/572,899, filed May 13, 2008 (Inventor—Karandikar et al.).
Restriction requirement issued on Jun. 28, 2011 for U.S. Appl. No. 11/572,899, filed May 13, 2008 (Inventor—Karandikar et al.).
Protest Documents from 3rd Party filed on Apr. 3, 2009 for U.S. Appl. No. 11/572,899, filed May 13, 2008 (Inventor—Karandikar et al.).
Preliminary Amendment filed on Jan. 29, 2007 for U.S. Appl. No. 11/572,899, filed May 13, 2008 (Inventor—Karandikar et al.).
Intl. Preliminary Report on Patentability issued on Jan. 30, 2007 for Intl. App. No. PCT/US05/027261 filed Aug. 1, 2005, published Mar. 9, 2006 as WO 06/026026 (Applicant—Acrymed, Inc.).
Intl. Search Report with Written Opinion issued on Apr. 28, 2006 for Intl. App. No. PCT/US05/027261 filed Aug. 1, 2005, published Mar. 9, 2006 as WO 06/026026 (Applicant—Acrymed, Inc.).
Notice of Acceptance issued on Jan. 24, 2011 for AU Pat. App. No. 2005280443, which claims priority to Intl. Pat. App. No. PCT/US05/027261, filed on Aug. 1, 2005, published on Mar. 9, 2006 as WO 06/02026 (Applicant—Acrymed, Inc.).
Response to Examiner's Report filed on Dec. 13, 2010 for AU Pat. App. No. 2005280443, which claims priority to Intl. Pat. App. No. PCT/US05/027261, filed on Aug. 1, 2005, published on Mar. 9, 2006 as WO 06/02026 (Applicant—Acrymed, Inc.).
Examiner's First Report issued on Feb. 19, 2010 for AU Pat. App. No. 2005280443, which claims priority to Intl. Pat. App. No. PCT/US05/027261, filed on Aug. 1, 2005, published on Mar. 9, 2006 as WO 06/02026 (Applicant—Acrymed, Inc.).
AU Divisional App. No. 2011202034 filed on May 3, 2011 from AU Pat. App. No. 2005280443, which claims priority to Intl. Pat. App. No. PCT/US05/027261, filed on Aug. 1, 2005, published on Mar. 9, 2006 as WO 06/02026 (Applicant—Acrymed, Inc.).
Second Office Action (Text Portion) issued on Jun. 7, 2011 for Chinese Pat. App. No. 200580028877.0, which claims priority to Intl. Pat. App. No. PCT/US05/027261, filed on Aug. 1, 2005, published on Mar. 9, 2006 as WO 06/02026 (Applicant—Acrymed, Inc.).
Response to Office Action filed on Jul. 9, 2009 for Chinese Pat. App. No. 200580028877.0, which claims priority to Intl. Pat. App. No. PCT/US05/027261, filed on Aug. 1, 2005, published on Mar. 9, 2006 as WO 06/02026 (Applicant—Acrymed, Inc.).
First Office Action issued on Dec. 26, 2008 for Chinese Pat. App. No. 200580028877.0, which claims priority to Intl. Pat. App. No. PCT/US05/027261, filed on Aug. 1, 2005, published on Mar. 9, 2006 as WO 06/02026 (Applicant—Acrymed, Inc.).
Response to Examiner's Report filed on Jun. 30, 2011 for Indian Pat. App 397/KOLNP/2007, which claims priority to Intl. Pat. App. No. PCT/US05/027261, filed on Aug. 1, 2005, published on Mar. 9, 2006 as WO 06/02026 (Applicant—Acrymed, Inc.)—proposed amendments only.
Examiner's Report issued on Jul. 2, 2010 for Indian Pat. App 397/KOLNP/2007, which claims priority to Intl. Pat. App. No. PCT/US05/027261, filed on Aug. 1, 2005, published on Mar. 9, 2006 as WO 06/02026 (Applicant—Acrymed, Inc.).
Official Action issued on Mar. 1, 2011 for JP App. No. 2007-523881, which claims priority to Intl. Pat. App. No. PCT/US05/027261, filed on Aug. 1, 2005, published on Mar. 9, 2006 as WO 06/02026 (Applicant—Acrymed, Inc.)—translation included.
Notice of Acceptance issued on Apr. 26, 2011 for New Zealand Pat. App. No. 552928, which claims priority to Intl. Pat. App. No. PCT/US05/027261, filed on Aug. 1, 2005, published on Mar. 9, 2006 as WO 06/02026 (Applicant—Acrymed, Inc.).
Response to Examination Report filed on Apr. 21, 2011 for New Zealand Pat. App. No. 552928, which claims priority to Intl. Pat. App. No. PCT/US05/027261, filed on Aug. 1, 2005, published on Mar. 9, 2006 as WO 06/02026 (Applicant—Acrymed, Inc.).
Examination Report issued on Feb. 2, 2011 for New Zealand Pat. App. No. 552928, which claims priority to Intl. Pat. App. No. PCT/US05/027261, filed on Aug. 1, 2005, published on Mar. 9, 2006 as WO 06/02026 (Applicant—Acrymed, Inc.).
Response to Examination Report filed on Jan. 20, 2011 for New Zealand Pat. App. No. 552928, which claims priority to Intl. Pat. App. No. PCT/US05/027261, filed on Aug. 1, 2005, published on Mar. 9, 2006 as WO 06/02026 (Applicant—Acrymed, Inc.).
Further Examination Report issued on Jul. 8, 2010 for New Zealand Pat. App. No. 552928, which claims priority to Intl. Pat. App. No. PCT/US05/027261, filed on Aug. 1, 2005, published on Mar. 9, 2006 as WO 06/02026 (Applicant—Acrymed, Inc.).
Response and Amended Pages filed on Jun. 28, 2010 for New Zealand Pat. App. No. 552928, which claims priority to Intl. Pat. App. No. PCT/US05/027261, filed on Aug. 1, 2005, published on Mar. 9, 2006 as WO 06/02026 (Applicant—Acrymed, Inc.).
Examination Report issued on Apr. 24, 2009 for New Zealand Pat. App. No. 552928, which claims priority to Intl. Pat. App. No. PCT/

(56) References Cited

OTHER PUBLICATIONS

US05/027261, filed on Aug. 1, 2005, published on Mar. 9, 2006 as WO 06/02026 (Applicant—Acrymed, Inc.).
NZ Divisional App. No. 592438 filed on Apr. 21, 2011 from New Zealand Pat. App. No. 552928, which claims priority to Intl. Pat. App. No. PCT/US05/027261, filed on Aug. 1, 2005, published on Mar. 9, 2006 as WO 06/02026 (Applicant—Acrymed, Inc.).
Amendment Entered with CPA/RCE filed on Feb. 19, 2010 for U.S. Appl. No. 11/194,951, filed Aug. 1, 2005 (Inventor—Karandikar et al.).
Notice of Appeal filed on Oct. 21, 2009 for U.S. Appl. No. 11/194,951, filed Aug. 1, 2005 (Inventor—Karandikar et al.).
Final Rejection issued on May 21, 2009 for U.S. Appl. No. 11/194,951, filed Aug. 1, 2005 (Inventor—Karandikar et al.).
Response After Non-Final Rejection filed on Feb. 5, 2009 for U.S. Appl. No. 11/194,951, filed Aug. 1, 2005 (Inventor—Karandikar et al.).
Non-Final Rejection issued on Aug. 5, 2008 for U.S. Appl. No. 11/194,951, filed Aug. 1, 2005 (Inventor—Karandikar et al.).
Response to Election / Restriction filed on Feb. 5, 2008 for U.S. Appl. No. 11/194,951, filed Aug. 1, 2005 (Inventor—Karandikar et al.).
Requirement for Restriction/Election issued on Dec. 5, 2007 for U.S. Appl. No. 11/194,951, filed Aug. 1, 2005 (Inventor—Karandikar et al.).
Examiner's first report issued on Oct. 18, 2010 for Australian Pat. App. No. 2007215443, which claims priority to PCT/US07/03390, filed Feb. 8, 2007, published on Aug. 23, 2007 as WO 07/095058 (Applicant—Acrymed, Inc.).
Third Office Action issued Jul. 7, 2011 for Chinese Pat. App. No. 200780012684.5, which claims priority to PCT/US07/003390 filed on Feb. 8, 2007 (Applicant—AcryMed, Inc.).
Response to Second Office Action filed on Jun. 7, 2011 for Chinese Pat. App. No. 200780012684.5, which claims priority to PCT/US07/003390 filed on Feb. 8, 2007 (Applicant—AcryMed, Inc.)—No Translation.
Second Office Action issued Mar. 23, 2011 for Chinese Pat. App. No. 200780012684.5, which claims priority to PCT/US07/003390 filed on Feb. 8, 2007 (Applicant—AcryMed, Inc.).
Response to First Office Action filed on Feb. 28, 2011 for Chinese Pat. App. No. 200780012684.5, which claims priority to PCT/US07/003390 filed on Feb. 8, 2007 (Applicant—AcryMed, Inc.)—Proposed amended claims in English.
First Office Action issued Oct. 13, 2010 for Chinese Pat. App. No. 200780012684.5, which claims priority to PCT/US07/003390 filed on Feb. 8, 2007 (Applicant—AcryMed, Inc.).
Supplemental European Search Report issued May 23, 2011 for EP App. No. 07750244.1, which claims priority to PCT/US07/03390, filed Feb. 8, 2007, published on Aug. 23, 2007 as WO 07/095058 (Applicant—Acrymed, Inc.).
Claim amendments filed on Sep. 4, 2008 for EP App. No. 07750244.1, which claims priority to PCT/US07/03390, filed Feb. 8, 2007, published on Aug. 23, 2007 as WO 07/095058 (Applicant—Acrymed, Inc.).
PCT Preliminary Report on Patentability issued on Aug. 12, 2008 for Intl. Pat. App. No. PCT/US07/03390, filed Feb. 8, 2007, published on Aug. 23, 2007 as WO 07/095058 (Applicant—Acrymed, Inc.).
PCT Intl. Search Report with Written Opinion issued on Dec. 21, 2007 for Intl. Pat. App. No. PCT/US07/03390, filed Feb. 8, 2007, published on Aug. 23, 2007 as WO 07/095058 (Applicant—Acrymed, Inc.).
Non-Final Rejection issued on Jun. 30, 2011 for U.S. Appl. No. 11/704,167, filed Feb. 8, 2007 (Inventors—Karandikar et al.).
Amendment Entered with CPA/RCE filed on Apr. 22, 2011 for U.S. Appl. No. 11/704,167, filed Feb. 8, 2007 (Inventors—Karandikar et al.).
Final Rejection issued on Dec. 22, 2010 for U.S. Appl. No. 11/704,167, filed Feb. 8, 2007 (Inventors—Karandikar et al.).
Response after Non-Final Action mailed Oct. 28, 2010 for U.S. Appl. No. 11/704,167, filed Feb. 8, 2007 (Inventors—Karandikar et al.).
Non-Final Rejection issued on May 28, 2010 for U.S. Appl. No. 11/704,167, filed Feb. 8, 2007 (Inventors—Karandikar et al.).
Response to Election / Restriction filed on Apr. 30, 2010 for U.S. Appl. No. 11/704,167, filed Feb. 8, 2007 (Inventors—Karandikar et al.).
Restriction/Election Requirement issued on Mar. 30, 2010 for U.S. Appl. No. 11/704,167, filed Feb. 8, 2007 (Inventors—Karandikar et al.).
Preliminary Amendments filed on Nov. 24, 2008 for EP 07755996.1 which claims priority to PCT/US07/009997, filed on Apr. 25, 2007, published on Nov. 8, 2007 as WO 07/127236 (Applicant—Acrymed, Inc.).
Intl. Search Report w/ Written Opinion issued on Aug. 25, 2008 for Intl. Pat. App. No. PCT/US07/009997, filed on Apr. 25, 2007, published on Nov. 8, 2007 as WO 07/127236 (Applicant—Acrymed, Inc.).
Intl. Preliminary Report on Patentability issued on Oct. 28, 2008 for Intl. Pat. App. No. PCT/US07/009997, filed on Apr. 25, 2007, published on Nov. 8, 2007 as WO 07/127236 (Applicant—Acrymed, Inc.).
Final Rejection issued on Jun. 23, 2011 for U.S. Appl. No. 11/789,701, filed Apr. 25, 2007 (Inventors—McMaken et al.).
Response after Non-Final Rejection filed on Apr. 5, 2011 for U.S. Appl. No. 11/789,701, filed Apr. 25, 2007 (Inventors—McMaken et al.).
Non-Final Rejection issued on Oct. 5, 2010 for U.S. Appl. No. 11/789,701, filed Apr. 25, 2007 (Inventors—McMaken et al.).
Amendment Entered with CPA/RCE filed on Mar. 31, 2010 for U.S. Appl. No. 11/789,701, filed Apr. 25, 2007 (Inventors—McMaken et al.).
Final Rejection issued on Oct. 5, 2009 for U.S. Appl. No. 11/789,701, filed Apr. 25, 2007 (Inventors—McMaken et al.).
Response After Non-Final Rejection filed Jun. 8, 2009 for U.S. Appl. No. 11/789,701, filed Apr. 25, 2007 (Inventors—McMaken et al.).
Non-Final Rejection issued on Jan. 26, 2009 for U.S. Appl. No. 11/789,701, filed Apr. 25, 2007 (Inventors—McMaken et al.).
Response to Election / Restriction filed on Dec. 15, 2008 for U.S. Appl. No. 11/789,701, filed Apr. 25, 2007 (Inventors—McMaken et al.).
Requirement for Restriction/Election issued on Nov. 14, 2008 for U.S. Appl. No. 11/789,701, filed Apr. 25, 2007 (Inventors—McMaken et al.).
Intl. Preliminary Report on Patentability issued on May 24, 2011 for Intl. Pat. App. No. PCT/US09/065764, filed on Nov. 24, 2009, published on May 27, 2010 as WO 10/060094 (Applicant—Kimberly-Clark, Worldwide Inc..).
Intl. Search Report with Written Opinion issued on Apr. 28, 2010 for Intl. Pat. App. No. PCT/US09/065764, filed on Nov. 24, 2009, published on May 27, 2010 as WO 10/060094 (Applicant—Kimberly-Clark, Worldwide Inc.).
Reply to Communication from Examining Division filed on Jun. 16, 2011 for EP App. No. 05797894.2, which claims priority to PCT/US05/033600, filed Sep. 19, 2005, published on Mar. 30, 2006 as WO 06/034249 (Applicant—Acrymed, Inc.).
Communication from Examining Division issued on Feb. 8, 2011 for EP App. No. 05797894.2, which claims priority to PCT/US05/033600, filed Sep. 19, 2005, published on Mar. 30, 2006 as WO 06/034249 (Applicant—Acrymed, Inc.).
Reply to Communication from Examining Division filed on Jun. 23, 2009 for EP App. No. 05797894.2, which claims priority to PCT/US05/033600, filed Sep. 19, 2005, published on Mar. 30, 2006 as WO 06/034249 (Applicant—Acrymed, Inc.).
Communication from Examining Division issued on Dec. 17, 2008 for EP App. No. 05797894.2, which claims priority to PCT/US05/033600, filed Sep. 19, 2005, published on Mar. 30, 2006 as WO 06/034249 (Applicant—Acrymed, Inc.).
Supplemental European Search Report and Opinion issued on Oct. 21, 2008 for EP App. No. 05797894.2, which claims priority to PCT/US05/033600, filed Sep. 19, 2005, published on Mar. 30, 2006 as WO 06/034249 (Applicant—Acrymed, Inc.).

(56) References Cited

OTHER PUBLICATIONS

Amendments before examination filed on Apr. 18, 2007 for EP App. No. 05797894.2, which claims priority to PCT/US05/033600, filed Sep. 19, 2005, published on Mar. 30, 2006 as WO 06/034249 (Applicant—Acrymed, Inc.).

Intl. Preliminary Report on Patentability issued on May 1, 2007 for Intl. Pat. App. No. PCT/US05/033600, filed Sep. 19, 2005, published Mar. 30, 2006 as WO 06/034249 (Applicant—Acrymed, Inc.).

Intl. Search Report with Written Opinion issued on Apr. 18, 2007 for Intl. Pat. App. No. PCT/US05/033600, filed on Sep. 19, 2005, published on Mar. 30, 2006 as WO 06/034249 (Applicant—Acrymed, Inc.).

Final Rejection issued on Jun. 13, 2011 for U.S. Appl. No. 11/663,236, filed Mar. 19, 2007 (Karandikar et al.).

Response after Non-Final Action filed on Apr. 12, 2011 for U.S. Appl. No. 11/663,236, filed Mar. 19, 2007 (Karandikar et al.).

Non-Final Rejection issued on Dec. 13, 2010 for U.S. Appl. No. 11/663,236, filed Mar. 19, 2007 (Karandikar et al.).

Response to Restriction/Election Requirement filed on Sep. 23, 2010 for U.S. Appl. No. 11/663,236, filed Mar. 19, 2007 (Karandikar et al.).

Restriction/Election Requirement issued on Jun. 23, 2010 for U.S. Appl. No. 11/663,236, filed Mar. 19, 2007 (Karandikar et al.).

Preliminary Amendment filed on Mar. 19, 2007 for U.S. Appl. No. 11/663,236, filed Mar. 19, 2007 (Karandikar et al.).

Milk Composition & Synthesis Resourse Library, Milk Composition-Minerals [retrieved on Dec. 5, 2010], retrieved from the internet: <URL:http://ciasses.ansci.illinois.edu/ansc438/milkcompsynth/milkcomp_minerals.html>.

OxyGenesis Dissolved Oxygen Dressings: Case Review, AcryMed, Inc., Jan. 23, 2010.

Pepe, R.C, Wenninger, J.A., & McEwen, G.N., eds., Int'l Cosmetic Ingredient Dictionary & Handbook, 9th ed., 2002, vol. 2. pp. 177.

Price, William R. et al., "Silver Nitrate Burn Dressing, Treatment of Seventy Burned Persons," American Journal of Surgery, 1966, 112:674-680.

Ratner, Buddy D. et al., ACS Symposium Series, No. 31, The American Chemical Society, Synthetic Hydrogels for Biomedical Applications, pp. 1-36, 1976.

Rifai et al., "Facile in Situ Silver Nanoparticle Formation in Insulating Porous Polymer Matrices," Chemistry of Materials 2006; 18(1): 21-25.

Roe, David F., Gibbins, Bruce L., and Ladizinsky, Daniel A., "Topical Dissolved Oxygen Penetrates Skin: Model and Method," J Surg Res. 2010, 159(1):e29-e36.

Russel A. and Hugo, W., "Antimicrobial Activity and Action of Silver," Progress in Medicinal Chemistry, vol. 31, G-.P. Ellis & D.K. Luscombe, ed., Elsevier Science B.V., 1994; pp. 351-370.

Schacht, Etienne H., Hydrogel Drug Delivery Systems, Institute of Organic Chemistry, State University Gent, 1984, pp. 259-278.

Sheehan et al, "Anti-bacterial Silver Coatings on Orthopaedic Metals—An In Vitro and Animal Study," Journal of Bone and Joint Surgery. 2003, 85-B(Supp_II):141.

* cited by examiner

OXYGEN-DELIVERY CLOSED CELL FOAM MATRIX FOR WOUND TREATMENT

PRIOR RELATED APPLICATIONS

The present application relies on the priority of U.S. Provisional Patent Application No. 60/174,024, filed Dec. 30, 1999, herein incorporated in its entirety.

FIELD OF THE INVENTION

The present invention relates generally to the field of materials for the delivery of gases and other agents in the treatment of compromised tissues. More particularly, the present invention relates to treatment of compromised tissues using devices comprising novel matrix materials, comprising either synthetic or natural materials, wherein such novel materials are capable of encapsulating gas bubbles to form a device that transfers the gas to a receiving substrate.

BACKGROUND OF THE INVENTION

Damage or destruction of the blood supply to a region of living tissue quickly leads to compromised tissue. One of the critical functions of an adequate blood supply is the provision of dissolved gases to the site, such as oxygen. For example, wounds to bodily tissues are accompanied by damage or destruction of the natural blood supply that transports oxygen and nutrients that are necessary to support the healing process. Measurements have shown that the tissue oxygen tension within the wound and surrounding damaged tissues is substantially lower than the normal blood vascular oxygen tension. Whereas the blood vascular oxygen level of 80 to 100 mm Hg is considered normal, the wound environment may have as little as 3 to 30 mm Hg of oxygen. Research has shown that a level of 30 mm Hg or less is insufficient to support the processes of wound repair.

Many approaches have been used in an effort to increase the amount of oxygen delivered to compromised tissues. Initial developments to increase the oxygen tension in the compromised tissue environment involved either topical delivery of oxygen to the tissues or chambers in which the blood vascular oxygen tension is substantially elevated so as to also increase to tissue oxygen levels by diffusion. U.S. Pat. No. 4,328,799 describes a hyperbaric oxygen chamber that was constructed such that it fit tightly to a portion of the anatomy. The chamber was then flooded with oxygen gas to higher than atmospheric pressure to increase dissolution of oxygen for delivery to cellular processes. U.S. Pat. Nos. 4,474,571, 4,624,656, and 4,801,291 further describe various improvements for increasing the atmospheric oxygen concentration over the compromised tissue environment. Although these devices are capable of functionally increasing the oxygen level over a wound site, they suffer from the use of cumbersome apparatus, intermittent delivery of oxygen and poor transfer of oxygen from the oxygen-rich atmosphere to the hypoxic tissues.

Another device, disclosed in U.S. Pat. No. 4,608,041, combined delivery of oxygen to tissues with providing an escape pathway for spent gas and wound-derived volatiles. U.S. Pat. No. 4,969,881 extended this development to use less bulky construction by utilizing an oxygen permeable membrane sandwich in which the interior portion was flooded with oxygen which diffused through the wound contact membrane, but not the upper membrane, to oxygenate tissues. This was further improved in U.S. Pat. No. 6,000,403. These devices represent improvements that overcame much of the bulky characteristics of previous inventions but represent little or no improvement in the transfer of oxygen to hypoxic tissues nor do they constitute improvements in wound contact matrices customarily needed for wound care.

A different approach, used to increase the efficiency of the transfer of oxygen and to eliminate the bulky apparatus was to use nascent oxygen generation near the device. U.S. Pat. No. 5,407,685 provides a device for generating oxygen when the device was applied to a wound. The device disclosed is a bilayered device where each layer contains a reactant that mixes and generates oxygen once exudate or other bodily-derived material activates the reaction. U.S. Pat. No. 5,736,582 describes the generation of oxygen from hydrogen peroxide for release at or near the skin surface. U.S. Pat. No. 5,855,570 similarly uses an electrochemical reaction to convert oxygen in air to a peroxide or other reactive form of oxygen for delivery to the wound environment. U.S. Pat. No. 5,792,090 uses a reservoir that contained hydrogen peroxide and a catalyst in a device in contact with the wound, such as a hydrogel or polymeric foam. Another approach was disclosed in U.S. Pat. No. 5,086,620 in which pure gaseous oxygen was dispersed by sonic energy into a liquid matrix that was then solidified by cooling to encapsulate the oxygen in minute bubbles.

These devices represent improvements in the delivery of topical oxygen to the wound environment over the hyperbaric chamber. However, each carries significant limitations that have restricted the broad adaptation of the technology of topical oxygenation for care of compromised tissues. Previously described devices do not have a known concentration of oxygen and cannot function independently of atmospheric pressures or temperature to achieve effective oxygen distribution. In addition, the dependence upon activation by body-derived agents is unpredictable so as to make such devices impractical. Other devices are expensive to produce and require specialized equipment. Such devices cannot be used in the production of cold set polymers that are often used for the construction of medical devices used for compromised tissue care.

Compromised tissues include those tissues that have an interrupted blood supply or suffer from a lack of a necessary element, such as oxygen, or suffer from the build-up of by-products, such as carbon dioxide. One type of compromised tissue includes wounds. Wounds are generally thought of as an interruption in the integrity of the skin. The outer layer of skin surrounding the body performs an important protective function as a barrier against infection, and serves as a means of regulating the exchange of heat, fluid and gas between the body and external environment. When skin is removed or damaged by being abraded, burned or lacerated, this protective function is diminished. Areas of damaged skin are conventionally protected by the application of a wound dressing which facilitates wound healing by acting as a skin substitute.

Compromised tissues can result from any interruption in normal biological activity in an area. Compromised tissues result from external insults such as friction, abrasion, laceration, burning or chemical irritation. Damage to such tissues may also result from internal metabolic or physical dysfunction, including but not limited to bone protrudence, diabetes, circulatory insufficiencies, or inflammatory processes. Normally, tissue damage initiates physiological processes of regeneration and repair. Generally, the repair process is uneventful and may occur regardless of any intervention. However, it has been found that intervention and provision of needed elements aid in repair of compromised tissue sites.

Another aspect of repair of the compromised site may include the control of exudates and the maintenance of an optimal level of moisture over the compromised site, especially during heavy exudate drainage.

The healing of compromised tissues usually progresses through distinct stages leading to the eventual restoration of the natural function. As an example, injury to the skin initiates an immediate vascular response characterized by a transient period of vasoconstriction, followed by a more prolonged period of vasodilation. Blood components infiltrate the wound site, endothelial cells are released, exposing fibrillar collagen, and platelets attach to exposed sites. As platelets become activated, components are released which initiate events of the intrinsic coagulation pathway. At the same time, a complex series of events trigger the inflammatory pathways generating soluble mediators to direct subsequent stages of the healing process. These events result in a transient to prolonged period of oxygen deprivation known as hypoxia in the tissues.

Normally, the healing process of injured tissues is uneventful and may occur regardless of any intervention. However, where an underlying metabolic condition or perpetual insult such as pressure is a contributing factor, the natural healing process may be retarded or completely arrested, resulting in a chronic wound. Trends in modern medical practices have shown that the wound healing of both acute and chronic wounds may be significantly improved by clinical interventions using methods and materials that optimize conditions in the compromised tissues to support the physiological processes of the progressive stages of tissue repair. In dermal wounds, key factors in providing the optimal conditions are the prevention of scab formation and the maintenance of an optimal level of moisture and oxygen in the wound bed. All of these factors may be controlled by the management of wound exudate fluid.

A common problem in the management of both acute and chronic wounds is the maintenance of an optimal level of moisture over the wound bed during heavy exudate drainage. This is usually, but not always, during the early stage of healing. Most moist wound dressing technologies such as thin films, hydrocolloid dressings and hydrogels are typically overwhelmed by exudate moisture during this heavy drainage phase. Management of moisture during heavy exudate drainage often necessitates the use of gauze or sponge packings that wick away excess moisture from the wound bed, thin film coverings that trap exudate fluid over the wound bed, calcium, alginate dressings that chemically bind exudate moisture due to the hydroscopic properties of the seaweed extract and other materials that generally restrict exposure to atmospheric oxygen to the wound site.

Prior Art Dressings

Soluble collagen has been used as a subcutaneous implant for repairing dermatological defects such as acne scars, glabellar furrows, excision scars and other soft tissue defects. Collagen has also been used in many forms as wound dressings such as collagen sponges, as described in Artandi, U.S. Pat. No. 3,157,524 and Berg et al., U.S. Pat. No. 4,320,201. However, most of these dressings are not satisfactory for the various types of compromised tissues. Collagen films and sponges do not readily conform to varied wound shapes. Furthermore, some collagen wound dressings have poor fluid absorption properties and undesirably enhance the pooling of fluids.

Another example of dressings that have been developed are hydrocolloid dressings. UK Patent No. 1,471,013 and Catania et al., U.S. Pat. No. 3,969,498 describe hydrocolloid dressings that are plasma soluble, form an artificial eschar with the moist elements at the wound site, and gradually dissolve to release medicaments. Hydrocolloid dressings in general, and the Catania et al. dressings in particular, are subject to a number of drawbacks. The major disadvantages of these dressings include the potential to disintegrate in the presence of excess fluid at the site, and minimal, virtually negligible, control over water and/or oxygen loss from the wound. This latter disadvantage is particularly important, as excess water loss from a wound will cause an increase in heat loss from the body as a whole, potentially leading to hypermetabolism. In addition, hydrocolloid dressings require frequent dressing changes.

Some treatments for compromised tissues can cause problems at the sites. For example, thin film dressings such as those described in U.S. Pat. No. 3,645,835, maintain excessive moisture over a wound bed, contributing to the overhydration or maceration of surrounding skin. Although sponges and gauze support tissue, they require frequent changing, and cause irritation to the compromised tissues during body movement and dressing removal. Calcium alginates turn into a gelatinous mass during interaction with moisture, are difficult to remove completely, and often dehydrate a wound bed due to the hydroscopic nature of the matrix. In addition, none of these devices or materials contribute to maintaining an appropriate level of oxygen to the compromised tissue site. Nor do any of the currently available devices significantly contribute to or support the autolytic debridement phase of wound healing.

Delivery of Active Agents

Another desirable aspect of treatment of compromised tissues is the delivery of active agents to the site of injury. Active agents for use in compromised tissue treatment may be administered to an individual in a variety of ways. For example, active agents may be administered via methods known to those skilled in the art, such as topically, sublingually, orally, or by injection (subcutaneous, intramuscular or intravenous). Nevertheless, there are drawbacks to many of these methods, and an inexpensive, reliable, localized and relatively pain-free method of administering active agents has not been provided in the prior art.

One common method employed for the treatment of compromised tissues is the topical application of a salve or ointment. Topical application to a wound can be painful. Additionally, in the case of a deeply cavitated wound, an excess of active agent may be required because the agent must diffuse through layers of necrotic tissue and newly forming epidermal tissues. Furthermore, application of topical agents to sites in the interior of the body is highly impractical in that the topical agents are washed off or migrate to other sites. This difficulty in delivering the agent may require the application of an excessive amount of the agent and preclude an accurate determination of the effective amount of active agent delivered.

The oral and sublingual administrations of active agents used in wound treatment also have their drawbacks. Ingestion of an active agent may result in the agent having negative system-wide effects and possibly disturbing the normal flora, or normal microbial environment, whose presence benefits an individual. Successful absorption of the agent into the bloodstream also depends on several factors such as the agent's stability in gastrointestinal fluids, the pH of the gastrointestinal tract, solubility of solid agents, intestinal motility, and gastric emptying.

Injection of an active agent, a normally painful method of administration, may have the same negative system-wide effects as that of an oral or sublingual administration. Yet more importantly, a danger inherent in the injection of an active agent is that rapid removal of the agent is impossible once it is administered. There is also a risk of transmission of infections and the possibility of vascular injury due to the use of needles.

Therefore, topical, oral, sublingual and intravenous methods of administration pose several problems when delivering active agents for the treatment of compromised tissues. What is needed is a method of administering an active agent for the treatment of compromised tissue in an effective, safe and relatively pain-free manner.

What is needed therefore, are methods and compositions for improving treatments for compromised tissue comprising materials having superior exudate management capabilities, together with the ability to deliver active therapeutic agents and participate in the management of oxygen tension around such sites. Methods and compositions are needed that can provide oxygen delivery to any size area of compromised tissue and preferably, may also provide moisture control and delivery of other active agents.

In addition, there continues to be a need for a device such as a wound dressing that possesses high moisture absorption capacity, a high rate of absorption, as well as a capacity to regulate moisture at the wound bed-dressing interface. Desirably, such a wound dressing device should stimulate the autolytic debridement process, especially during the heavy exudating phase of wound care management.

SUMMARY OF THE INVENTION

The present invention is directed to compositions, methods and devices comprising contact tissue materials for delivery of gases and other active agents. A preferred embodiment of the present invention comprises compositions and methods for the treatment of compromised tissue. In particular, the present invention provides methods and compositions for providing gases, preferably oxygen, to a site of compromised tissue or to any site where delivery of the gas is desired. Such sites include, but are not limited to, compromised tissue such as ischemic or hypoxic tissue or wounds. A preferred embodiment comprises the delivery of oxygen, which is important in methods such as keeping cells, tissues, organs or animals alive, such as in packaging of live fish, or tissue culture vessels.

Preferred embodiments of the present invention are directed to methods and devices for treatment of compromised tissue, such as ischemic or hypoxic tissue or wounds. In one embodiment of the present invention, a tissue contact material is provided that delivers oxygen locally to the wound site and may also allow for localized delivery of other active agents and control of moisture and debridement. Such a tissue contact material can be used as a wound dressing to treat wounds.

In preferred embodiments of the present invention, methods and compositions are provided that comprise a material and a process for making a novel material that contains an entrapped gas, preferably gaseous oxygen. The material may comprise a natural or synthetic polymer that forms a closed cell foam structure. Preferably, the cells of the foam are highly enriched for gaseous oxygen and the walls of the foam cells are enriched for dissolved oxygen. This material is useful as a primary tissue contact matrix where it is desirable to transfer oxygen into the tissue environment to increase the oxygen tension. A preferred embodiment is a polyacrylate matrix that is also flexible, elastic, conformable and highly absorbent comprising an optimal wound dressing matrix.

Other substrates comprising formations of closed cell foams for the delivery of oxygen to tissues are contemplated by the present invention. For example, natural polymers of gelatin, dextrose, collagen, agar and agarose possess necessary molecular architecture for the encasement of gases such as oxygen within closed cells to form a foam-like structure. These natural polymers have the added advantage in that they are absorbed by the tissues over time thus eliminating the requirement for removal once the active agent has been exhausted. Therefore, these materials may be implanted into deep tissue sites.

Similarly other water swellable cross-linked polymers such as polyacrylate, polymethacrylamide, polyester, polyether and polyurethane can entrap gases such as oxygen in close cell reservoirs within the matrix for delivery to compromised tissues. Furthermore, certain water non-swellable polymers such as silastic and silicone elastomer polymers may entrap gases such as oxygen within closed cell structures.

The methods, compositions and devices of the present invention may be used to simultaneously deliver at least one active agent to a site. Agents such as antimicrobial agents, antifungal agents, antiviral agents, growth factors, angiogenic factors, anaesthetics, mucopolysaccharides and other proteins may be incorporated into the compositions and devices for release into the environment. Especially preferred compositions and devices comprise a matrix that delivers both oxygen and another active agent that has enhanced activity because of the presence of the oxygen. For example, certain therapeutic agents are relatively inactive under reducing conditions but become significantly more active when conditions become more oxygenated. Adjuvants and other agents, such as those that boost the immune system, may also be incorporated into the devices of the present invention. A surprising and novel aspect of embodiments having agents directly incorporated into micro-cavities of the matrix is that the activities of the agents are not altered by incorporation into the devices and that the agents are effective upon their release.

In a further preferred embodiment, the devices of the present invention comprise a stranded configuration, wherein the strands extend from at least one common region and the strands themselves comprise a polyacrylate matrix. In a preferred embodiment of the present invention, wound dressing devices of the present invention comprise novel stranded structures made from a matrix suitable for application to broken skin and underlying tissues. The individual strands of the preferred embodiment may or may not have free floating ends, however, the unique arrangement of the device allows it to maintain optimal oxygen tension around a wound site, absorb excess wound exudate, and simultaneously conform closely to the walls of the wound bed, in order to accelerate overall wound healing. In addition to oxygen tension management, increased moisture absorption and the ability to deliver active agents, the individual strands of the devices may participate in mechanical debridement thereby accelerating the wound healing process. Additionally, preferred devices may be left in place for prolonged periods between changes.

Accordingly, it is an object of the present invention to provide compositions and methods for the delivery of oxygen.

Another object of the present invention is to provide compositions, methods and devices for the treatment of compromised tissue.

A further object of the present invention is to provide compositions, methods and devices comprising materials that enable the management of oxygen tension in a localized environment.

Still another object of the present invention is to provide devices that deliver oxygen to contacted tissues.

It is another object of the present invention to provide compositions, methods and devices that absorb excess moisture at a site.

Yet another object of the present invention is to provide compositions, methods and devices comprising incorporation of active agents.

It is another object of the present invention to provide compositions, methods and devices that promote autolytic debridement of compromised tissues such as wounds.

A further object of the present invention is to provide compositions, methods and devices for external and internal compromised tissues.

Another object of the present invention is to prevent infection by providing compositions, methods and devices that clean wound sites by removing debris and contaminating material.

Still a further object of the present invention is to prevent infection by providing compositions, methods and devices that provide oxygen to anerobic sites.

In yet another object of the present invention, compositions, methods and devices are provided that deliver active agents, with or without the delivery of oxygen, to compromised tissue sites, for the prevention of infection and to aid in healing.

Another object of the present invention is to provide compositions, methods and devices that deliver oxygen for the enhancement of the activity of active or therapeutic agents.

Yet another object of the present invention is to provide compositions, methods and devices that deliver oxygen so that living organisms are kept alive.

Still a further object of the present invention is to provide compositions, methods and devices that deliver oxygen to tissues and organs that are removed from their original source, such as tissues and organs that are used for transplants.

A further object of the present invention is to provide compositions, methods and devices that deliver oxygen for packaging and shipping purposes.

It is another object of the present invention to provide compositions, methods and devices that easily conform to the shape of a compromised tissue site.

It is yet another object of the present invention to provide compositions and devices that are easily manufactured.

Still another object of the present invention is to provide compositions, methods and devices that may be easily removed from compromised tissues and replaced.

Yet another object of the present invention is to provide compositions, methods and devices that are compatible with injured tissue and do not induce irritation or inflammation.

It is yet another object of the present invention to provide compositions, methods and devices that function to both absorb wound exudate and promote autolytic debridement.

Another object of the present invention is to provide compositions and methods for making single unit construction devices having multiple strands.

It is another object of the present invention to provide methods and compositions for treating compromised tissues using devices that function to both absorb moisture, deliver oxygen and deliver active agents.

An object of the present invention to provide methods and compositions for treating wounds using wound dressing devices having active agents incorporated therein.

Still another object of the present invention is to provide methods and compositions for delivering active agents to wound sites and damaged tissue.

A further object of the present invention is to provide tissue contact material that entraps gaseous oxygen or other gases to form a closed cell foam.

It is another object of the present invention to provide an oxygen-delivering tissue contact material that may be resorbed by tissues.

These and other objects, features and advantages of the present invention will become apparent after a review of the following detailed description of the disclosed embodiments and the appended claims.

DETAILED DESCRIPTION

Figure 1:
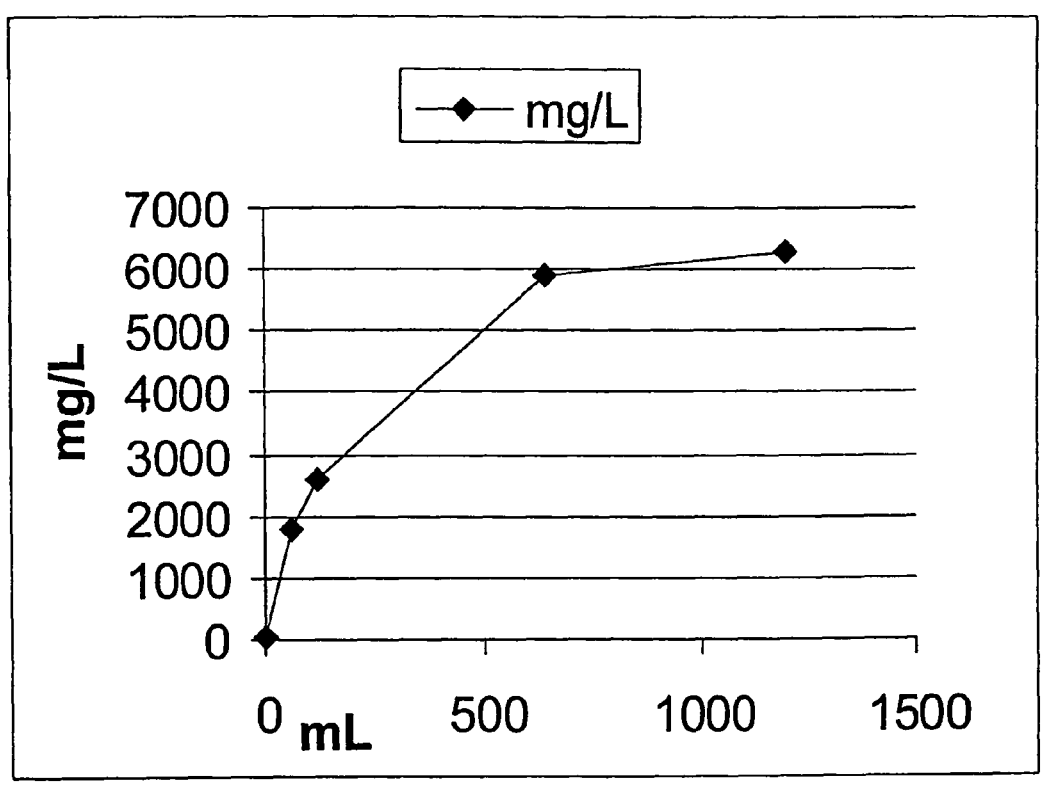
FIG. 1 is a graph demonstrating the results of an experiment conducted to develop a method of determining total oxygen present in foamed oxygen dressing. The graph shows that as a greater volume of distilled water is used for oxygen extraction, the calculated total oxygen concentration reaches a plateau of approximately 6268.6 ppm.

The present invention comprises compositions, methods and devices for the delivery of gases, preferably oxygen, or other active agents, to a localized environment. Preferred embodiments of the present invention comprise devices comprising matrices that can deliver known amounts of oxygen. The preferred embodiments are used in methods of treatment of compromised tissues and for methods of preserving life and maintaining the state of extracted tissues or organs.

The present invention comprises compositions, methods and devices for the treatment of compromised tissues. A preferred embodiment of the present invention comprises compositions and methods for treating compromised tissue comprising tissue contact materials that entrap oxygen within closed cell foam-like material capable of providing or maintaining optimal oxygen tension at a compromised tissue site while absorbing excess fluid and optimizing the microenvironment to facilitate tissue repair and regeneration if needed. In addition, preferred devices of the present invention have superior wound exudate/moisture absorption capabilities. In certain embodiments of the present invention, the methods, compositions and devices further comprise active agents incorporated therein for release at the site. In a further preferred embodiment, the matrix composition comprises a polymer network with a non-gellable polysaccharide dispersed evenly throughout the network. The matrices of this preferred embodiment provide a reliable and efficient means for maintaining oxygen tension, delivering active agents to the wound while at the same time providing a superior moisture regulation capacity. In still another embodiment of the invention, the polymer is a bioresorbable polymer suitable for topical and for implantation applications.

The tissue contact material devices of the present invention are not restricted by form or shape. The devices may be constructed in sheet style formats of various dimensions.

Similarly, the materials can be molded to conform to various shapes and contours as required by the intended use. Preferred embodiments of the present invention, particularly those used as wound dressing devices, may also take a particular conformation. For example, a preferred embodiment of the present invention comprises a stranded configuration wherein the individual strands extend from at least one common region and may have free floating ends. This particular conformation is particularly suitable for use in deeply cavitated wounds since the multiple matrix strands enable the dressing to conform to individual and uniquely shaped wound areas. Furthermore, the devices accelerate wound healing by displacing and allowing for the removal of excess cellular exudate and debris, thereby improving the rate of tissue repair and regeneration.

DEFINITIONS

The terms "a", "an" and "the" as used herein are defined to mean one or more and include the plural unless the context is inappropriate.

The term "compromised tissue" as used herein can be one or more tissues and includes any organism, organ system, organ, tissue, cells or cellular components that is not in its normal metabolic state. For example, it means any tissue that has an abnormal blood supply, such as that caused by ischemic conditions, hypoxic conditions, infarction, occlusions, blockages, or trauma. It also includes wounds and damage to structural components.

The present invention is directed to compositions, methods and devices for the delivery of active agents, including gases. In particular, preferred embodiments are directed to delivery of oxygen to compromised tissue. An example of preferred embodiments for treatment of compromised tissues is the treatment of wounds. This example is for illustration, and should not be used in a limiting sense, and such preferred embodiments can be used for treatment of other types of compromised tissue.

In addition to the management of excess moisture and infection around a wound site, it is also important to maintain the appropriate oxygen tension around the wound in order to facilitate effective healing. Several studies have shown that whereas oxygen tension in normal, uninjured tissue is approximately 80 to 100 mm Hg, the tension in injured or damaged tissue is as low as 3 to 30 mm Hg. It has also been demonstrated that levels of oxygen below 30 mm Hg are insufficient to support the process of wound repair. The novel methods and compositions of the present invention provide unique tissue contact materials that enable not only the absorption and management of wound exudate and moisture, but importantly also enable the control of oxygen tension around a wound thereby facilitating efficient and superior tissue repair and regeneration. In alternative embodiments of the invention, the wound dressing device also comprises active therapeutic agents which are released and can be delivered in a controlled release manner. The release may be mobilized by a fluid phase that occurs as the matrix takes up moisture from the environment or the contact substrate.

A preferred embodiment of the present invention comprises a suspension of components for the formation of a polymer, such as acrylamide, together with various solvents such as lipids, water and alcohol. More particularly, a preferred composition comprises a water suspension containing acrylamide, bis acrylamide, glycerol, guar gum and isopropyl alcohol. The suspension is mixed to completely hydrate the guar gum and dissolve the other ingredients. Subsequently, a solution such as TEMED is sequentially added together with ammonium persulfate and sodium carbonate. The material is then mixed and poured into molds and allowed to gel. The gelled sheets are transferred into a drying oven for dehydration and are then rehydrated with a solution of hydrogen peroxide. After a 'rest period' of several hours, the foamed oxygen-containing material may then be cut to size and sterilized, for example, by electron beam irradiation.

A specifically preferred composition of the present invention is made according to the following method. To 42.5 g $H_2O$ add 2.47 g acrylamide, 0.03 g bis acrylamide, 2.5 g glycerol and 0.275 g guar gum suspended in 0.275 g isopropyl alcohol. Mix the suspension for 3 hours to completely hydrate the guar gum and dissolve the other ingredients. Sequentially add to the mixture 0.026133 ml TEMED, 0.368 g ammonium persulfate and 0.0888 g sodium carbonate. After 5 minutes of mixing the mixture is poured into sheet molds and allowed to gel. The gelled sheets are then transferred into a drying oven at 45-50° C. to dehydrate below 10% w/w moisture. The sheets are then rehydrated with a 10% solution of hydrogen peroxide at the ratio of 0.6 g sheet to 0.25 ml solution. The material is allowed to stand for 12 hours. The foamed oxygen containing material may then be cut to size and sterilized by electron beam irradiation.

The chemical reaction between the hydrogen peroxide (second reactant) and the carbonate catalyst (reactant) causes the formation of water and gaseous oxygen which in turn causes the formation of closed cells or bubbles within the matrix. The cells contain an enriched concentration of gaseous oxygen. The moisture in the walls of the matrix contain dissolved oxygen.

As is known to those of skill in the art, the components listed above in the preferred composition may be substituted by similar or equivalent materials. For example, the process may be carried out by substituting the carbonate reactant with other types of catalysts. Catalysts also include, but are not limited to, organic and inorganic chemicals such as cupric chloride, ferric chloride, manganese oxide, sodium iodide and their equivalents. Other catalysts, include, but are not limited to enzymes such as lactoperoxidase and catalase. Similarly, the second reactant, hydrogen peroxide, may be substituted with other peroxides, including, but not limited to, ammonium peroxide and sodium peroxide. The present invention contemplates use of components that can generate a gaseous element within the matrix and that are safe and effective for use. For example, an acid catalyst can be incorporated in the matrix followed by perfusion of the matrix with a carbonate to generate carbon dioxide gas within the matrix. Such materials are then used to buffer solutions or environments.

Further details concerning the methods and compositions of the present invention are found in the Examples below.

Active Agents

The active agents incorporated into the present invention are selected on the basis of the use of the device. Active agents and their effects are known by those skilled in the art and methods for including these agents into the matrices of the present invention are taught herein. The present invention contemplates the inclusion of one or more active agents, depending on the intended use. The compositions and devices may include one agent, such as oxygen, or may include multiple agents. For example, if the device is a matrix gel sheet placed in a tissue culture dish and is used to provide oxygen to the growing cells, the active agents include oxygen and any other agents that aid the cells, such as antimicrobials to maintain sterility, or growth factors to aid in cell growth.

If the devices are used for topical treatments, such as treatments for compromised tissues, the devices comprise active agents that aid in treatment of compromised tissues. For example, the devices are used for the treatment of wounds, in skin healing or for cosmetic applications. The active agents aid and improve the wound healing process, and may include gases, anti-microbial agents, including but not limited to, anti-fungal agents, anti-bacterial agents, anti-viral agents and anti-parasitic agents, mycoplasma treatments, growth factors, proteins, nucleic acids, angiogenic factors, anaesthetics, mucopolysaccharides, metals and other wound healing agents.

Active agents include, but are not limited to, gases, such as oxygen, nitrogen, carbon dioxide, and noble gases, pharmaceuticals, chemotherapeutic agents, herbicides, growth inhibitors, anti-fungal agents, anti-bacterial agents, anti-viral agents and anti-parasitic agents, mycoplasma treatments, growth factors, proteins, nucleic acids, angiogenic factors, anaesthetics, mucopolysaccharides, metals, wound healing agents, growth promoters, indicators of change in the environment, enzymes, nutrients, vitamins, minerals, carbohydrates, fats, fatty acids, nucleosides, nucleotides, amino acids, sera, antibodies and fragments thereof, lectins, immune stimulants, immune suppressors, coagulation factors, neurochemicals, cellular receptors, antigens, adjuvants, radioactive materials, and other agents that effect cells or cellular processes.

Examples of anti-microbial agents that can be used in the present invention include, but are not limited to, isoniazid, ethambutol, pyrazinamide, streptomycin, clofazimine, rifabutin, fluoroquinolones, ofloxacin, sparfloxacin, rifampin, azithromycin, clarithromycin, dapsone, tetracycline, erythromycin, ciprofloxacin, doxycycline, ampicillin, amphotericin B, ketoconazole, fluconazole, pyrimethamine, sulfadiazine, clindamycin, lincomycin, pentamidine, atovaquone, paromomycin, diclazaril, acyclovir, trifluorouridine, foscarnet, penicillin, gentamicin, ganciclovir, iatroconazole, miconazole, Zn-pyrithione, and silver salts such as chloride, bromide, iodide and periodate.

Growth factor agents that may be incorporated into compositions and devices of the present invention include, but are not limited to, basic fibroblast growth factor (bFGF), acidic fibroblast growth factor (aFGF), nerve growth factor (NGF), epidermal growth factor (EGF), insulin-like growth factors 1 and 2, (IGF-1 and IGF-2), platelet derived growth factor (PDGF), tumor angiogenesis factor (TAF), vascular endothelial growth factor (VEGF), corticotropin releasing factor (CRF), transforming growth factors $\alpha$ and $\beta$ (TGF-$\alpha$ and TGF-$\beta$), interleukin-8 (IL-8); granulocyte-macrophage colony stimulating factor (GM-CSF); the interleukins, and the interferons.

Other agents that may be incorporated into compositions and devices of the present invention are acid mucopolysaccharides including, but not limited to, heparin, heparin sulfate, heparinoids, dermatitin sulfate, pentosan polysulfate, chondroitin sulfate, hyaluronic acid, cellulose, agarose, chitin, dextran, carrageenan, linoleic acid, and allantoin.

Proteins that may be especially useful in the treatment of compromised tissues, such as wounds, include, but are not limited to, collagen, cross-linked collagen, fibronectin, laminin, elastin, and cross-linked elastin or combinations and fragments thereof. Adjuvants, or compositions that boost an immune response, may also be used in conjunction with the wound dressing devices of the present invention.

Other wound healing agents that are contemplated in the present invention include, but are not limited to, metals. Metals such as zinc and silver have long been known to provide excellent treatment for wounds. Delivery of such agents, by the methods and compositions of the present invention, provide a new dimension of care for wounds.

It is to be understood that in preferred embodiments of the present invention, the active agents are incorporated into compositions and devices so that the agents are released into the environment. In topical treatments, the agents are then delivered via transdermal or transmucosal pathways. The incorporated agents may be released over a period of time, and the rate of release can be controlled by the amount of cross-linking of the polymers of the matrices. In this way, the present invention retains its ability to affect the local environment, kill or inhibit microorganisms, boost the immune response, exert other alterations of physiological function and provide active agents over an extended period of time.

In another embodiment of the present invention, active agents are incorporated directly into micro-cavities of the matrix of the wound dressing devices. The agents may be incorporated by absorption of agents by the matrix, and preferably by incorporation during the polymerization of the matrix. It is theorized that the release of the active agents may be controlled via manipulation of concentration parameters, movement of water through the matrix and the degree of cross linking in the matrix.

Administering active agents for the treatment of compromised tissue by using the compositions and methods of the present invention overcomes several of the problems of the prior art. First, the present invention avoids the painful re-application of salves and ointments to compromised tissues. The present invention also allows active agents to be delivered directly to the site to prevent the negative impact of system-wide delivery of the agents. In the case of deeply cavitated wounds, in contrast to the topical application of active agents, wound dressing compositions and devices with active agents therein may be located directly within the wound, providing a more effective delivery of the agents. Finally, in contrast to an injection of active agents, the present invention provides methods of administering active agents wherein the agents may be removed immediately from the compromised tissue and the administration terminated.

Matrices

The present invention comprises a matrix material such as polyacrylamide and a non-gellable mucopolysaccharide, and most preferably, further comprises a catalyst (reactant) that generates a gas when reacted with another component (second reactant), and further comprises one or more active agents incorporated therein. A unique feature of the matrices of the present invention is the formation of the foam or array of bubbles that entrap the gas. The foam or bubbles are formed by the permeation of the second reactant added to the formed matrix that includes a reactant. When the two reactants interact, a reaction occurs that liberates gas which is entrapped within the matrix. For example, a matrix has a carbonate catalyst (a reactant) incorporated within it. The formed matrix is then placed in the presence of the second reactant, hydrogen peroxide. A catalytic decomposition of hydrogen peroxide occurs resulting in the liberation of oxygen gas which becomes entrapped as bubbles formed in situ. The hydrogen peroxide reactant is not part of the compounding of the matrix, but it is in the treatment after the formation of the matrix stock.

In preferred embodiments of the present invention, the matrix is flexible and elastic, and is a semi-solid scaffold that is permeable to substances such as aqueous fluids, inorganic salts, aqueous fluids and dissolved gaseous agents including oxygen. Though not wishing to be bound by any particular theory, it is thought that the substances permeate the matrix through movement via intermolecular spaces among the cross-linked polymer.

Preferably, the matrix material is constructed from natural or synthetic polymers. The matrix may also optionally include a non-gellable polysaccharide. Natural polymers that may be used include, but are not limited to collagen, gelatin, chondritin, calmodulin, cellulose, agar, agarose, animal hide, hyaluronic acid, dextran and alginate. Synthetic polymers that may be used include, but are not limited to polylysine and other resorbable polymers, polyacrylamide, polymethacrylate, polyacrylate, polybuterate, polyurethane foam, polyether, silastic, silicone elastomer, rubber, nylon, vinyl or cross-linked dextran. If cross-linked dextran is used, it is preferred that the molecular weight of the dextran polymer is between 50,000 and 500,000. Additionally, the matrix material can be made from a combination of natural and synthetic polymers, or mixtures of synthetic polymers or mixtures of natural polymers.

The most preferable non-gellable polysaccharide is a non-gellable galactomannan macromolecule such a guar gum. A concentration range of guar gum between approximately 0.005 to 53% w/w, preferably between approximately 0.05 to 5% w/w, and most preferably between approximately 0.25 to 1% w/w is generally sufficient. Other non-gellable polysaccharides may include lucerne, fenugreek, honey locust bean gum, white clover bean gum and carob locust bean gum.

To decrease the permeability of the matrix, water loss control agents may be applied to the surface of the device. Application of water loss control agents is preferred since a decrease in the permeability of the device controls the loss of fluids. The preferred water loss control agent is petrolatum, however, other water loss control agents such as glycolipids, ceramides, free fatty acids, cholesterol, triglycerides, sterylesters, cholesteryl sulfate, linoleic ethyl ester and silicone oil may also be used. Additionally, the compositions and devices may have an impermeable sheet covering one or more surfaces to aid in control of moisture.

If desired, a plasticizer may also be added to the matrix material. Preferred plasticizers include glycerol and water, however, propylene glycol and butanol may also be used. If glycerol is used, a range of between approximately 0.25 to 25% w/w, preferably between 0.5 to 12% w/w, and most preferably between approximately 2.5 to 8% w/w is generally sufficient. The plasticizer may be added in the initial mixture of polymer and cross-linking agent.

If desired, a hydration control agent may be incorporated into the matrix. The preferred hydration control agent is an isopropyl alcohol, however, ethanol, glycerol, butanol, and propylene glycol may also be used. A range of isopropyl alcohol of between approximately 0.05 to 5% w/w, preferably between approximately 0.1 to 2.5 w/w and most preferably between approximately 0.25 to 1% w/w is generally sufficient.

The matrix of a preferred embodiment preferably comprises polymerized chains of polyacrylamide, wherein the acrylamide monomers are cross-linked with a cross-linking agent, and a non-gellable polysaccharide and an active agent or pharmaceutical may become directly encapsulated into micro-cavities therein. A range of acrylamide between approximately 0.5 to 50% w/w, preferably between approximately 1 to 25% w/w, and most preferably between approximately 2.5 to 10% w/w is generally sufficient.

The most preferable cross-linking agent is N,N'-methylene-bisacrylamide, however other appropriate cross-linking agents such as bisacrylylycystamine and diallyltartar diamide may also be used. If N,N'-methylene-bisacrylamide is used, a range of between approximately 0.005 to 0.5% w/w, preferably between approximately 0.01 to 0.25 w/w, and most preferably between approximately 0.025 to 0.15 w/w is generally sufficient. Ammonium persulfate and TEMED may also be added to the matrix. A range of ammonium persulfate between approximately 0.005% to 0.5% w/w, preferably between approximately 0.01 to 0.25 w/w, and most preferably between approximately 0.025 to 0.1% w/w is generally sufficient. Additionally, a range of TEMED between approximately 0.001 to 0.5 w/w, preferably between approximately 0.01 to 0.25% w/w, and most preferably between approximately 0.025 to 0.15 w/w is generally sufficient.

A most preferred embodiment of the present invention comprises reactants used to create the bubbles or foam that entrap gas. These reactants can be catalysts that react with the second reactant to form the bubbles and entrap the gas. A most preferred reactant or catalyst is sodium carbonate. A range concentration of the reactant or catalyst is between approximately 0.005% to 10.0% w/w, preferably between approximately 0.01 to 5.0 w/w, and most preferably between approximately 0.1 to 5.0% w/w is generally sufficient. The most preferred concentration of sodium carbonate is approximately 1.0% w/w.

Incorporation of Active Agents

One embodiment of the matrices of the present invention can be found in U.S. Pat. No. 5,196,190 to Nangia et al., which is hereby incorporated in its entirety. Nangia et al. teach a matrix composed of a natural or synthetic polymer, a non-gellable polysaccharide, and a phospholipid based drug delivery system. In particular, Nangia et al. teach a matrix capable of drug delivery, wherein lipid vesicle liposomes containing a desired drug are incorporated into the matrix.

One problem with such a matrix, however, is the difficulty of incorporating active agents into the liposomes because some agents may be incompatible with liposome chemistry. Incorporation using liposomes is time consuming, expensive and sometimes unreliable because dispersion of the liposomes in the matrix is difficult to achieve and once achieved, the liposomes may prematurely release costly agents due the liposomes' inherent instability. Another problem is that the prior art fails to teach a method of incorporating active agents into a device wherein the release of the agent over time can be controlled through the manipulation of concentration parameters, movement of water through the matrix and the degree of cross linking in the matrix.

Preferred embodiments of the present invention however, address the need for a less expensive, quicker, and more reliable method for incorporating a wider range of desired agents into wound dressing devices. Preferred embodiments also provide a means to control the release of the desired agents over time via manipulation of concentration parameters, movement of water through the matrix and the degree of cross-linking in the matrix. In a preferred embodiment, the desired agents may be directly incorporated into the matrix by adding the agents into the initial formulation for the matrix prior to cross-linking. This method of incorporation is inexpensive, rapid and reliable, and most surprisingly, the incorporated agents are not affected by the process of polymerization and retain their biological activities. Additionally, active agents may be adsorbed or absorbed into a preformed matrix. Some embodiments have the second reactant and the active agent added to the preformed matrix, either simultaneously or sequentially, for perfusion within the matrix. The present invention also contemplates other methods of incorporation of active agents, such enclosed within liposomes or other vesicles, other methods known to those skilled in formulations for delivery of active agents.

Using preferred embodiments of the present invention, delivery of the desired agents may be controlled by the use of movement of liquid through the matrix. Though not wishing to be bound by any theory, it is theorized that the liquid in a matrix of polymer and non-gellable polysaccharide is either bound to the non-gellable polysaccharide or it is unbound in the polymer mass. Thus, it is theorized that the present invention uses the free liquid portion of the matrix as a general solvent and as a means to deliver desired agents. Soluble drugs are easily dissolved in the free liquid portion, however slightly soluble drugs are ground to a fine powder and may require the use of a wetting agent such as glycerol or isopropyl alcohol or a surfactant such as polysorbate, triton-X or sodium lauryl sulfate.

Once the desired active agent or agents are dispersed throughout the matrix, it is thought that a portion of the agent resides in the non-gellable polysaccharide, while another portion of the agent is dissolved in the free liquid phase and moves freely through the matrix. The ability of the agent to move freely throughout the matrix in the free liquid phase is useful in the agent delivery system of the present invention. Because the agent is dissolved in the free liquid phase, a concentration gradient of the active agent is created between the matrix and the moisture of the environment. Therefore, when the matrix is placed onto a moist surface, the soluble agent will move through the free liquid phase toward the agent-free moisture, resulting in the delivery of the agent. This movement of soluble agent further upsets the equilibrium between soluble and insoluble agents, and causes more agent to dissolve into the free liquid phase, thus causing more agent to be delivered. Because preferred embodiments of the present invention incorporate the desired agent directly into the matrix rather than incorporating the drug into other delivery vehicles such as liposomes, the agent may be dissolved in the free liquid phase and reliably delivered through the process described above. It is theorized that gaseous agents, such as oxygen, are dissolved in the liquid of the matrix and are released from the matrix. Additionally, the gases may be released directly into the air of the environment, enriching the environment.

Delivery of the desired agents may also be controlled by the degree of cross-linking in the matrix. As described above, the desired agents may be added to the other components forming the matrix, prior to the addition of the cross-linking agent. Subsequent addition of the cross-linking agent and concomitant polymerization results in both chain elongation of monomeric chemicals and cross-linking between chains of monomers. The combination of chains cross-linked together creates micro-cavities wherein the desired agents are encapsulated. By controlling the amount of cross-linking agent and the length of chains of monomer, it is possible to regulate the size of the micro-cavities in the polymer. Larger micro-cavities, produced by a lower degree of cross-linking, allow for freer migration and quicker delivery of the desired agent, whereas smaller micro-cavities increase the delivery time. Although the liposome-based delivery system may also make use of the degree of cross-linking, the liposome itself acts as an additional barrier to delivery, making delivery less controlled and less reliable than liposome-free delivery.

Stranded Structure

The compositions and devices of the present invention may take many physical forms, depending on uses of the compositions and devices. A preferred shape is a gel sheet that can be cut or molded into any two dimensional shape. Other preferred embodiments are primarily constructed of thin strands of matrix suitable for placement into the wound bed or cavity.

The preferred devices may be constructed from one or multiple strands of matrix. When multiple strands are used in the construction, the strands are secured together by wrap, tie, glue, or alternatively by a continuous bridge of matrix between adjacent strands. Multiple strands are secured together to minimize accidental loss during removal of the dressing from the wound bed. Typically, the strands of particular embodiments are bound or secured in the mid-region so that the ends of the device may float free. The advantage of free floating strands is to enable the individual strands to access a maximum volume of the wound and thereby absorb the excess fluid, exudate and debris. The mechanical action of the free floating strands contributes to the trapping and removal of cellular and wound debris. Concurrently the free floating strands also conform optimally with the contours of the wound surface to maximize contact between the device and the wound bed. See U.S. Pat. No. 5,928,174, herein incorporated by reference in its entirety.

The unique stranded embodiment is particularly desirable because it enables the device to maintain its integrity and also maximize the surface area to volume ratio of its matrix. This is important since the matrix may be an absorbent material where a high surface area to volume ratio increases the rate of absorption, without increasing the overall absorption capacity of the device.

In a preferred embodiment, the wound dressing is principally constructed of a "stranded" matrix, which allows for optimal contact between the strands and the wound area. In addition, the stranded matrix construction maximizes the overall flexibility and pliability of the dressing. In embodiments of the device where multiple strands are employed, the overall flexibility and conformational characteristics of the device are maintained by binding strands in only limited and restricted areas. Minimal binding of the strands prevents the formation of rigid areas and allows for the effective and optimal utilization of numerous strands in a single device without adversely diminishing contact with the surface of the wound bed.

Another advantage of the stranded matrix construction is the "semi-porous" quality of the wound dressing that allows for the removal of extraneous cellular matter resulting during the wound healing process. The air in the inter-strands area of the device serve as a reservoir of space that may be displaced allowing for the removal of excess materials such as exudate fluid, debridement product and cellular exudate from the wound bed. As this region fills, the device may swell to provide "support" to the wound bed and surrounding tissues. A wound constitutes damaged or "missing" tissue, and when tissue is missing, the surrounding tissue may "collapse" or sag into the void. "Support" in this context therefore, means the temporary filling of the void to hold the surrounding tissue in place where it should reside.

Removal of debridement product and cellular exudate is further facilitated by unbound, loose strands of the wound dressing devices. When placed upon a wound, the loose strands of the devices randomly orient in the wound bed where the thin filamentous strands and free floating ends contribute to mechanical debridement of necrotic slough. Since the strands are secured and bound in at least one region, a mechanical union is formed, ensuring that all strands and necrotic tissue accumulation in the inter-strand spaces are removed from the wound when the device is changed. By contributing to the removal of extraneous wound products and cellular debris, the wound dressing device permits cleaning of the wound which in turn prevents and decreases the possibility of infection and contamination.

A preferred stranded configuration of the present invention is particularly desirable because the novel design provides a high surface area to volume ratio to maximize interchange between the matrix and wound debris. The multiple strands of the preferred configuration provide maximal inter-strand space to serve as a reservoir for moisture, necrotic materials, or agents scheduled for delivery to the wound bed. The superior moisture absorption and regulation capacity of the preferred embodiment equip the wound dressing devices for use on heavily to moderately draining wounds.

In one embodiment, the wound dressing device is constructed from a matrix composed of an absorbent synthetic polyacrylate material. The rate of absorption of polyacrylate is significantly increased by cutting the material into strands, which increases the surface area to volume ratio. This also provides a greater surface area for the release of dissolved oxygen and other active agents from the device. Polyacrylate material is particularly suitable for the wound dressings of the present invention because it retains its integrity during interaction with wound exudate moisture, as well as with necrotic tissue and wound debris. The wound dressing device of the present invention does not dissolve, gel or otherwise disintegrate during application to the wound. The preferred matrix swells slightly during the absorption of moisture, causing the device to conform closely to the walls of the wound bed.

In a preferred embodiment, the polyacrylate matrix is cut into free-floating strands bound together through a matrix-bridge in the mid-region. This pattern of construction imparts a significantly high surface area to volume ratio for rapid moisture movement within the absorbent matrix.

Wound dressing devices of the present invention may be produced by cutting a desired design pattern from stock sheets of matrix material. For example, the material may be die-cut from stock sheets of an absorbent polyacrylate wound dressing material. The stranded cut-out may then be coated with an agent to prevent aggregation and tangling of the free floating strands. Coating agents that may be used include, but are not limited to, petrolatum, talcum, polyglycols, glycerol, propylene, glycol, vegetable oil, and animal oil. Following the steps of cutting and coating, the material may be sterilized using sterilization techniques known in the art such as gamma radiation, steam and heat sterilization, electron beam or chemical sterilization (such as by use of ethylene oxide).

A preferred composition of the present invention is a matrix comprising a polymer, a non-gellable polysaccharide, and one or more active agents incorporated therein. A more preferred matrix comprises an acrylamide polymer, guar gum, and one or more active agents incorporated therein. A most preferred matrix comprises an acrylamide polymer, guar gum, and a catalyst that will support the decomposition of hydrogen peroxide to cause the formation of closed cells containing oxygen in the matrix. In addition the preferred embodiment may have one or more active agents incorporated therein, and is formed into a stranded structure wherein the strands are secured by at least one common region.

The wound dressing devices of the present invention may be used on injured tissue and for bodily fluid drainages where control and management of fluid and secretions is desired along with the delivery of oxygen to the tissues. The term "bodily fluid," as used herein, includes, but is not limited to, saliva, gingival secretions, cerebrospinal fluid, gastrointestinal fluid, mucous, urogenital secretions, synovial fluid, blood, serum, plasma, urine, cystic fluid, lymph fluid, ascites, pleural effusion, interstitial fluid, intracellular fluid, ocular fluids, seminal fluid, mammary secretions, vitreal fluid, and nasal secretions.

In particular, the wound dressing devices of the preferred embodiments are especially applicable for usage on heavily exudating acute and chronic wounds for controlling accumulating exudate moisture, support of the wound bed and surrounding tissues and supplying oxygen. Importantly, the wound dressings are particularly effective for stimulating and supporting autolytic debridement, inhibiting the growth of anaerobic bacteria and therefore accelerating the wound healing process.

In use, the wound dressing devices of the present invention are the primary dressing placed in direct contact with the wound bed, or as near as practical against the wound bed. The devices may serve as a packing material and, if required, may be secured into position with any suitable secondary wound dressing such as a wrap, tape, gauze, or pad. The dressings are temporary, however, and are not intended for permanent incorporation into the healed tissues. When necessary, the wound dressing devices are changed by first removing any over-dressing material and then removing the device, whereby any accumulated necrotic tissue and exudate is lifted away. The wound dressing devices of the present invention may be replaced by a fresh device or other suitable wound covering.

Additionally, wound dressing devices or contact tissue material devices of the present invention may be made of resorbable materials, such as polylysine or natural polymers. These devices may be left in place and are then resorbed by the body, instead of being removed. Such devices can comprise active agents, such as gases or other agents such as pharmaceutical or anesthetic agents.

The devices may be placed in their entirety into a wound, placed in combination with additional bundles of the same design into the wound, or cut through the bridge between strands to reduce the size or number of strands present in the wound.

The devices of the present invention may be cut, shaped and modified to accommodate numerous uses and applications. For example, the devices may be used as a gastric retrievable device, wherein a retrieval cord is attached to the device that is then swallowed. After absorption has taken place, the devices may be retrieved and analyzed for content.

The devices may undergo a swelling action as they absorb exudate moisture, however, they will not dissolve or disintegrate. The swelling action displaces necrotic material from the wound surface and forces the material into the inter-strands regions of the device. The laden moisture content and the retention of moisture near the wound bed by the invention contributes to stimulation of the autolytic debridement process whereby the body's own enzymes break-up necrotic tissue and cellular debris. Complete removal of the device occurs due to the conjoined nature of the device.

Other uses of the present invention include treatments for compromised tissues. The compositions and devices of the present invention, comprising tissue contact material, may comprise a gas, such as oxygen in an oxygen delivery function to replace some or all of the oxygen lost in the compromised tissue. Compositions and devices that comprise a gas delivery function, such as oxygen, and comprise other active agents are used to provide oxygen and other necessary agents, such as growth factors, nutrients or prevent infections or immune destruction in the compromised tissues.

The present invention is used to deliver gases, preferably oxygen, to any desired environment. Such an environment may be a tissue culture vessel. For example, a sheet of the matrix of the present invention comprising oxygen can be added to the tissue culture vessel and the matrix will release oxygen, allowing for the growth of the tissue culture. Oxygen-delivery matrices can be used to deliver oxygen to aquatic organisms that are trapped within a closed environment. Addition of an oxygen-containing matrix provides a steady source of oxygen for the organisms and prevents their death from suffocation. Additionally, oxygen-delivery matrices can be used to maintain oxygen levels in transplant organs or tissues and prevent their decay. For example, once the organ is removed, such as a kidney or heart donation, the organ is wrapped in a sheet of an oxygen-delivery matrix, placed in a cold environment and transported to the site where the transplant will occur.

The matrices of the present invention can deliver gases to organisms in need of such gases. For example, hydroponic plants can be provided with carbon dioxide or oxygen by the same or different matrices placed within the environment. Matrices can be placed in surrounding air or water environments. Provision of gases using the matrices of the present invention has applications for use in outer space. Matrices can be placed where delivery is desired and can be used for regular or emergency situations.

Oxygen-delivery matrices can be used to provide oxygen to anaerobic environments. In the presence of the matrix, anaerobic organisms will be killed, providing treatments for infections due to anaerobic organisms. One use for an oxygen-delivery devices such as the present invention, is in the control and elimination of strict anaerobic bacteria. Anaerobic bacteria have low or no tolerance for elemental oxygen and rapidly die if exposed to air or any other source of the gas. Pathogenic strains of these organisms tend to form localized anaerobic environments in tissues. The insertion of the present invention into such environments would serve to oxygenate the surrounding areas and thereby cause the death of the pathogens. Therefore, such a device has utility in the treatment of infectious gangrene.

Additionally, the oxygen supplied can be used to activate active agents that are not very active without oxygen and thus, these agents can be used in anaerobic environments. One or more matrices can be used to provide both the oxygen and the agent activated by the oxygen to allow for treatments of tissues that are not normally treated in this manner. One use for a tissue contact material for the delivery of oxygen to compromised tissues is in adjunctive therapies that might be enhanced in activity by an elevation of the local oxygen tension. As an example, certain therapeutic agents are relatively inactive under reducing conditions but become significantly more active when conditions become more oxygenated. The present invention therefore could be used to deliver a bolus of oxygen to the local environment such as the gut, vagina, or buccal cavity to enhance the activity of a therapeutic agent.

Other uses for provision of oxygen are contemplated by the present invention. Descriptions of uses provided herein are not to be limiting, but are illustrative of the many applications of the present invention. Other uses for the present invention include providing oxygen at a dental site, or around a surgical site or an infarct site. Transportation of living organisms or biological specimens includes the need to supply oxygen and the present invention is used in such a manner. For example, fish in an enclosed environment are maintained by a matrix of the present invention with oxygen incorporated therein. Other transport needs, such as for transplant organs or for chemicals that can be safely transported in the presence of an oxygen-rich environment, in the presence of other gases that can be provided by the presence of a matrix, is contemplated by the present invention.

All patents and patent applications disclosed herein are hereby incorporated by reference in their entirety. All references listed or cited herein are incorporated by reference in their entirety. U.S. Pat. No. 5,928,174 issued on Jul. 27, 1999, along with U.S. patent application Ser. No. 09/191,223 filed on Nov. 13, 1998, and U.S. Provisional Patent Application Ser. No. 60/157,000 filed on Oct. 1, 1999 are incorporated herein.

The foregoing description includes the best presently contemplated mode of carrying out the invention. This description is made for the purpose of illustrating the general principles of the inventions and should not be taken in a limiting sense. This invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention.

EXAMPLES

Example 1

Preparation of Oxygen-Containing Closed Cell Foam Device

The following experiment was conducted to make an oxygen containing closed cell foam device out of polyacrylamide matrix. More specifically the experiment involved use of hydrogen peroxide catalyzed by iodide in polyacrylamide matrix to form oxygen foam.

ACRYDERM® matrix material is a unique matrix that is water absorbent, elastic, and oxygen permeable (see U.S. Pat. No. 5,928,174). In order to elevate oxygen levels in the matrix for use as an oxygen donator, some treatment must be done post-polymerization, as oxygen quenches the polymerization of polyacrylamide. As demonstrated below, this was accomplished by allowing hydrogen peroxide to be absorbed into the matrix, where it contacted a decomposition catalyst and formed oxygen cavities.

Experimental Design:
1) A batch of ACRYDERM® matrix material was made incorporating 1% sodium iodide pre-polymerization. To 42.5 g $H_2O$ add 2.47 g acrylamide, 0.03 g bis acrylamide, 2.5 g glycerol and 0.275 g guar gum suspended in 0.275 g isopropyl alcohol. Mix the suspension for 3 hours to completely hydrate the guar gum and dissolve the other ingredients. Sequentially add to the mixture 0.026133 ml TEMED, 0.368 g ammonium persulfate and sodium iodide to make 1% w/w. After 5 minutes of mixing the mixture is poured into sheet molds and allowed to gel. The gelled sheets are then transferred into a drying oven at 45-50° C. to dehydrate to 10% to 20% of the original weight. The sheets are then re-hydrated with a solution of hydrogen peroxide, which causes the formation of the gas which is trapped in the matrix.
2) After polymerization and drying of the matrix, an excess of 3% hydrogen peroxide was added to one piece (Matrix A), and a few drops of hydrogen peroxide was added to another (Matrix B).
3) Matrices were observed for foam formation.

Results

Hydrogen peroxide was quickly absorbed by the matrices and began foaming.

Matrix A: violent bubbling→large bubbles in matrix, white closed cell foam formed as an end product Matrix B: uniform small closed cells formed in the matrix.

Matrix B had better uniformity in bubble formation than Matrix A. However there was a NaI residue and yellow (yellow very slowly fades) coloration presumably due to the catalyst used.

Hydrogen peroxide was decomposed by iodide to water and oxygen, and iodine gas was released.

Conclusion

Bubbles, highly enriched for oxygen, can be formed in the elastic polyacrylamide matrix by formulating the matrix with a hydrogen peroxide decomposition catalyst and then allowing the polymerized matrix to absorb hydrogen peroxide. The resulting reaction traps oxygen in the matrix. It is desired to have no residuals of this process left in the device, so an iodide to iodine gas decomposition is ideal due to the exodus of iodine gas from the device. Properties of the oxygenated device can be altered according the amount of peroxide applied.

Example 2

Comparison of Matrices Formulated with Alternative Peroxide Catalysts

The following experiment was conducted to make closed cell foam devices using hydrogen peroxide and alternative catalysts to sodium iodide.

It has been demonstrated that a closed cell foam incorporating oxygen bubbles can be made using iodide as a hydrogen peroxide decomposition catalyst. However, the catalytic reaction results in iodine gas formation, which does not dissipate quickly and leaves an odor. Also, residual sodium iodide in the device is not desired. Therefore, a decomposition catalyst that left either harmless residuals or no residuals was desirable.

Experimental Design
1) 3 control ACRYDERM® matrices were used.
2) Each was treated as follows: Soak 1 in a solution of cupric chloride to bring the final concentration to 2%. Soak 1 in a solution of ferric sulfate to bring the final concentration to 2%. Soak 1 in a sodium carbonate solution.
3) Soak each matrix in excess 3% hydrogen peroxide.
4) Observe matrices for foam formation, water solubility, moisture uptake, and volume increase.
5) Test matrices 11 days later for residual hydrogen peroxide using peroxidase assay.

Results

2% cupric chloride treatment→violent bubbling, destroyed matrix and matrix became water soluble.
2% ferric chloride treatment→bubbling, hard crusty dark brown, matrix became water soluble.
Sodium carbonate→good, quick foam formation
   X volume change=about 42 times larger than start size.
   Moisture uptake=8.923 times original weight when placed overnight in excess water.
   Water solubility=not water soluble
   Peroxide residue test=negative Conclusion If the decomposition of hydrogen peroxide was too strong, polyacrylamide was degraded. This can be avoided by lowering the amount of hydrogen peroxide used or using an alternative decomposition catalyst, such as sodium carbonate. Sodium carbonate as a catalyst formed a suitable foam, and decomposed into carbon dioxide gas, which is an acceptable residual.

Example 3

Rate of Release of Oxygen from Matrices into Water Substrate

The following experiment was conducted in order to test the rate of release of oxygen from foamed devices into water using a membrane dissolved oxygen electrode and meter.

As discussed above, topical application of oxygen to compromised tissue benefits healing. Theoretically, oxygen in the foamed matrix dissolves in the membrane moisture or exudate and enters the compromised tissue as dissolved oxygen. An in vitro simulation of this type of environment may be manufactured using water sealed in a bottle to prevent the escape or ingress of gases.

Experimental Design

The following steps were followed:
1) Place 0.7 mL 10% hydrogen peroxide on 0.6 g of a previously made matrix that incorporates 1% sodium carbonate.
2) 24 hrs later, place some of the foamed matrix in 110 mL distilled water in a sealed glass bottle excluding any air bubbles.
3) A dissolved oxygen probe was inserted in the bottle with a stir bar and sealed excluding air.
4) Under stirring, dissolved oxygen in ppm was recorded over time. After the readings peak, open the lid on the bottle and monitor until oxygen levels regain equilibrium.
5) As a control, repeat the same procedure, using 1% sodium carbonate device non-foamed, or 350 µL 10% hydrogen peroxide solution in place of the foamed device.

Results

| | Oxygen Matrix | | | | | | | |
|---|---|---|---|---|---|---|---|---|
| min | 0 | 4 | 5 | 22 | 25 | 32 | 24 hr open | 4 day open |
| DO | 8.4 | 9.5 | 10 | 13.5 | 14 | 15+ | 15+ | equil |
| | Hydrogen peroxide control | | | | | | | |
| min | 0 | 20 | 40 | 60 | 175 | | | |
| DO | 8.6 | 8.5 | 8.3 | 8.3 | 8.2 | | | |
| | 1% carbonate device control | | | | | | | |
| min | 10 | 20 | 40 | 60 | 160 | | | |
| DO | 8.6 | 8.5 | 8.3 | 8.3 | 8.2 | | | |

Conclusion

Oxygen rapidly was transferred from the foamed oxygen device to the substrate. The controls demonstrated that residual catalyst or hydrogen peroxide was not responsible for this increase. The foamed oxygen-delivery matrix delivered oxygen to the local environment, and maintained high oxygen levels in the substrate for at least a 24 hour period.

Example 4

Determination of Total Oxygen Content in Oxygen-Delivery Devices

The following experiment was conducted in order to develop a method of determining total oxygen present in the foamed oxygen devices.

In order to be an effective oxygen donator to tissue, the oxygen device must demonstrate that it can maintain release of oxygen over extended time periods. One indicator of the sustained release potential of the device was a calculation of the overall amount of oxygen present in the device. The dissolved oxygen probe used for testing has a maximum dissolved oxygen reading of 15 ppm. Since the delivery of oxygen from the device had greatly exceeded this level in previous experiments, a larger quantity of substrate (distilled water) should be used to determine total oxygen.

Experimental Design

The following steps were performed.
1) Obtain 5 0.3 g pieces of oxygen-delivery matrix made previously by placing 0.5 mL 10% hydrogen peroxide on 0.6 g pieces of 1% sodium carbonate ACRYDERM® matrix.
2) Place each device in sealed glass containers of various sizes with distilled water, excluding air bubbles (1200 mL, 635 mL, 120 mL, 60 mL).
3) At t=24 hrs, record the dissolved oxygen in each bottle with the membrane electrode dissolved oxygen meter, under stirring.
4) Calculate the total oxygen present in the device in ppm.

Results

| mL | DO | ppm | |
|---|---|---|---|
| 1200 | 10.4 | 6268.6 | |
| 635 | 11.8 | 5926.66 | |
| 120 | 15.5 | 2600 | |
| 60 | 18 | 1800 | |
| .3 | 44 | 44 | theoretical maximum solubility of oxygen in water |
| C | 9 | 0 | |

The results of this experiment are graphically provided in FIG. 1.

Conclusion

As the dissolved oxygen content approached 44 ppm (maximum solubility), the test chamber became more resistant to equilibration. As a greater volume of distilled water was used for the oxygen extraction, the calculated total oxygen concentration reached a plateau at levels considered to be accurate. Therefore, total ppm oxygen in the device was slightly greater than 6268.6 ppm for the formulation used.

Example 5

Oxygen Concentration Matrix Accomplished by Varying Peroxide Concentrations

The following experiment was conducted in order to demonstrate that oxygen devices may be made with different oxygen concentrations.

Varying the concentration of catalyst and hydrogen peroxide causes variation in a range of physical characteristics. In order to optimize the device's properties for use in different environments, it is advantageous to be able to adjust the oxygen concentration of the oxygen-delivery device.

Experimental Design

The following steps were followed:
1) Prepare 3 1% sodium carbonate ACRYDERM® matrix pieces.
2) To a 0.6 g piece of each, add 0.5 mL 3% hydrogen peroxide, 10% hydrogen peroxide, or 30% hydrogen peroxide to make three foamed matrices.
3) 1 day after manufacture, place 0.28 g pieces of foamed matrix in a sealed glass bottle with 600 mL distilled water, excluding air bubbles.
4) Also add 3.75 cm×2 cm pieces of matrix to 250 mL distilled water.
5) At t=24 hrs, take dissolved oxygen readings under stirring.

Results

| | | Oxygen/g | | | |
|---|---|---|---|---|---|
| ID | g device | mL water | 24 hr ppm | mg total | ppm total |
| 3% | .28 | 600 | 10.7 | 1.02 | 3642 |
| 10% | .28 | 600 | 13.4 | 2.64 | 9428 |
| 30% | .28 | 600 | 16 | 4.2+ | 15000+ |
| c | .28 | 600 | 9.0 | 0 | 0 |

| | Oxygen/cm$^2$ | | | |
|---|---|---|---|---|
| ID | area cm$^2$ | mL water | 24 hr ppm | mg total | mg/cm$^2$ |
| 3% | 7.5 | 250 | 11.3 | .575 | .076 |
| 10% | 7.5 | 250 | 12.4 | .85 | .113 |
| 30% | 7.5 | 250 | 13.1 | 1.025 | .1366 |
| c | NA | 250 | 9.0 | 0 | 0 |

Conclusion

By changing the concentration of hydrogen peroxide added to the device, a range of oxygen concentrations was achieved. A greater difference in concentrations was seen in the per gram experiment, due to the fact that an increase in oxygen is tied to an increase in volume of the device. However, on a per square area basis, a difference in oxygen concentrations was also attained.

Example 6

Rate of Release of Oxygen into Various Substrates (ABS/Saline/Water)

The following experiment was conducted in order to measure the rate of release of oxygen into various substrates.

Previous experiments demonstrated that oxygen is rapidly donated to water from the oxygen-delivery device. However, generally other environment are more complex than distilled water, and are more difficult to replicate in vitro. Two substrates tested were saline and mammalian blood serum.

Experimental Design

The following steps were followed:
1) Obtain three foamed oxygen matrices made as follows: 0.5 mL 10% hydrogen peroxide on 0.6 g 1% sodium carbonate device. Area=6×3 cm.
2) Prepare 3 250 mL glass bottles with distilled water, saline=0.85% NaCl, or adult bovine serum.
3) Place 0.3 g oxygen device in bottle and monitor dissolved oxygen. Bottle sealed with probe and stir bar, no air bubbles.

Results

Figure 2:
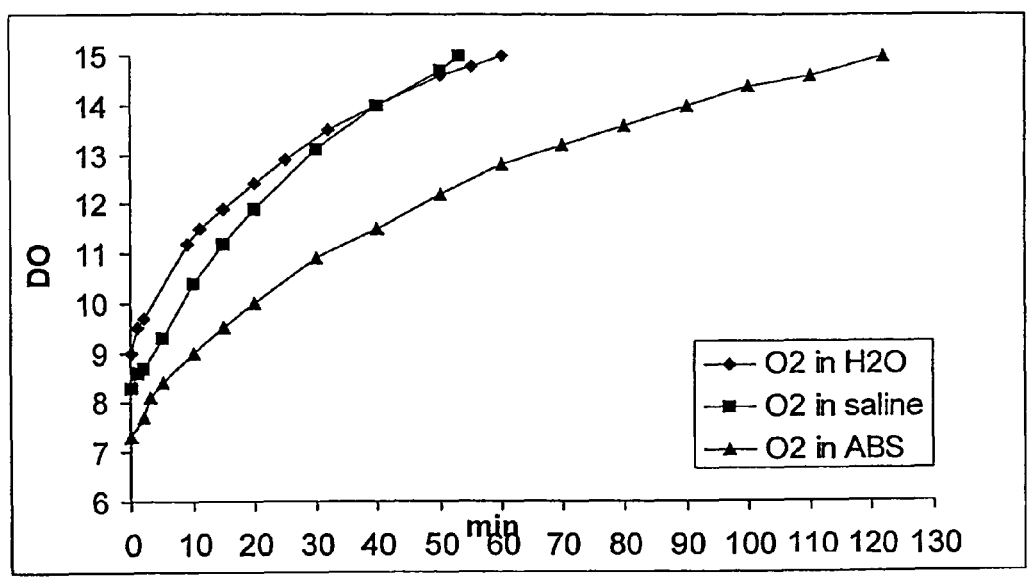
FIG. 2 is a graph showing the rate of release of oxygen into various substrates (water, saline and ABS) over time.

The results of this experiment are graphically provided in FIG. 2 showing dissolved oxygen in ppm over time.

Conclusion

Although differences existed in the rate of release of oxygen into various substrates, the rate of donation into more complex media was still rapid. Equilibrium dissolved oxygen concentrations were lower in the presence of salinity and other ions, explaining the lower initial dissolved oxygen levels and the slower rise in dissolved oxygen.

Example 7

Extending the Life of a Goldfish in a Sealed Container with Oxygen-Delivery Device The following experiment was conducted in order to determine whether oxygenated matrix can donate biologically relevant amounts of oxygen.

Preliminary work has shown that closed cell foam formation resulted from a combination of hydrogen peroxide and a peroxide degradation catalyst. The closed cell foam should contain nearly pure oxygen gas. Experiments using an oxygen detecting probe strongly supported that conclusion. Further testing was necessary to confirm that the foamed matrix was capable of donating biologically relevant oxygen. One approach was to show that the matrix can sustain the life of a fish in water held in a sealed bottle.

Experimental Design
The following steps were followed:
1) Place three weighed goldfish in 250 mL bottles distilled water.
2) At t=0, place 1 g oxygen-delivery device in one bottle and seal all bottles excluding air bubbles.
3) When one of the control goldfish dies (no oxygen-delivery matrix), open both control bottles, place 1 g oxygen device in the second control goldfish's bottle, (fish was dying), reseal with no bubble.
4) Observe all goldfish for time of death and read dissolved oxygen.
Results
Place goldfish in water 8:30 am, 11/9/99.

| Gold-fish | mL water | wt g | g ox device | death | death hrs | final ppm |
|---|---|---|---|---|---|---|
| 1 | 250 | 7.48 | 1 | 3:30 am 11-10 | 19:00 | 2.5 |
| 2 | 250 | 6.75 | 0 | 3:05 pm 11-9 | 6:35 | 2.5 |
| 3 | 250 | 8.63 | 0 | 4:30 pm 11-9 | 8:00 | 2.5 |

Figure 3:
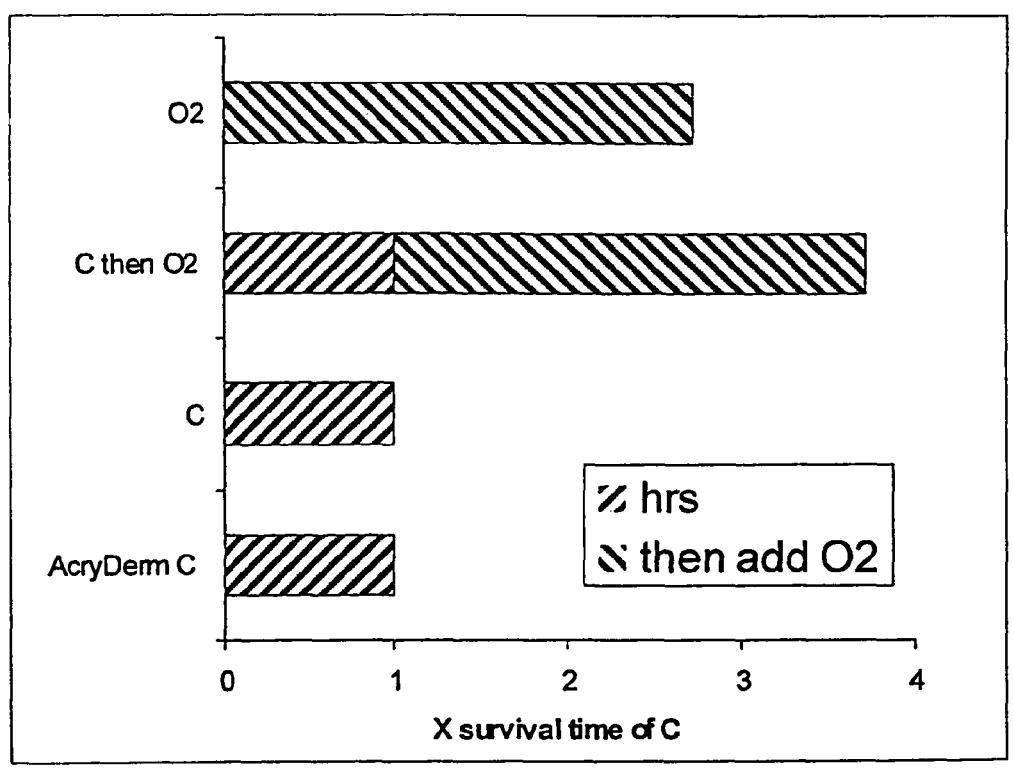
FIG. 3 is a graph showing the results of an experiment conducted in order to determine whether an oxygenated matrix can donate biologically relevant amounts of oxygen. In particular, the graph provides the survival time of goldfish in various sealed containers, with or without oxygen dressings.
Figure 4:
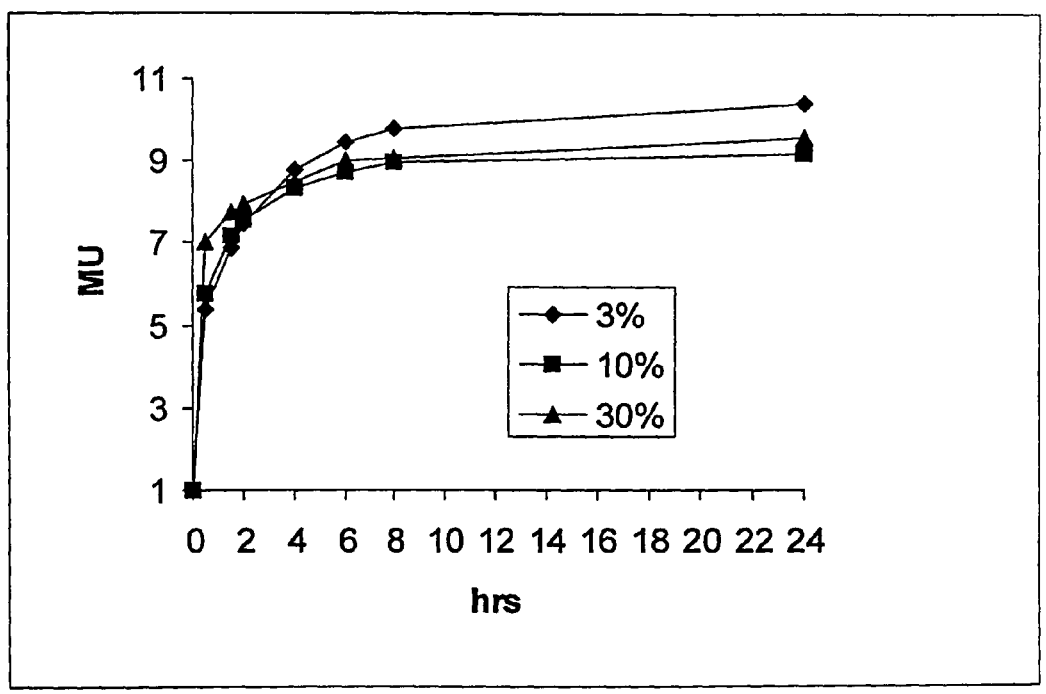
FIG. 4 is a graph showing moisture uptake of different formulations of oxygenated dressings.

Add 1 g oxygen device to #2 at 3:05 pm 11-9, dead 10:00 am 11-10→death hrs=25:30
Results The results of this experiment are graphically provided in FIG. 3 showing survival time of goldfish in a sealed container, with or without oxygen device (1=7 hrs)

Conclusion

Dissolved oxygen delivered by the foamed oxygen matrix was sufficient to sustain the life of a goldfish for an extended period of time. The goldfish with oxygen-delivery matrix survived approximately 3.5 times longer than a goldfish with no oxygen device. This indicated that the oxygen-delivery matrix can donate oxygen to living tissue in therapeutic doses over a desired time period.

Example 8

Moisture Uptake of Different Formulations of Oxygen-Delivery Device

The following experiment was conducted in order to determine moisture uptake properties of oxygen-delivery devices.

It has been shown that the foamed oxygen device can be manufactured to contain varying levels of oxygen. A rise in oxygen concentration coincided with volume growth and a drop in density of the device. It was desired to determine that increased oxygen content does not affect moisture uptake qualities in an adverse fashion.

Experimental Design
The following steps were followed:
1) Prepare 3 1% sodium carbonate ACRYDERM® matrix material devices as described in Example 1, except that instead of sodium iodide, 0.0888 g sodium carbonate is added, to make sodium carbonate at 1% w/w. The polymer mixture is allowed to gel, then dehydrated to approximately 20% of its original weight. The sample is then rehydrated with the hydrogen peroxide solution to allow formation of the oxygen gas and bubbles in the matrix.
2) To a 0.6 g piece of each, add 0.5 mL 3% hydrogen peroxide, 10% hydrogen peroxide, or 30% hydrogen peroxide to make three foamed devices.
3) Record weight and area of oxygen devices.
4) Immerse 3.6×4 cm samples of each device in 100 mL saline, incubate at 35° C. for 30 min.
5) Remove excess moisture by paper towel, weigh and record, return device to saline incubation.
6) Repeat weighing procedure at 1.5, 2, 4, 6, 8, and 24 hrs.
Results
Moisture uptake over time in grams

| ID | 0 hr | .5 hr | 1.5 hr | 2 hr | 4 hr | 6 hr | 8 hr | 24 hr |
|---|---|---|---|---|---|---|---|---|
| 3% | .5914 | 3.163 | 4.07 | 4.42 | 5.17 | 5.58 | 5.78 | 6.17 |
| 10% | .2726 | 1.572 | 1.94 | 2.06 | 2.27 | 2.37 | 2.44 | 2.50 |
| 30% | .1294 | .9076 | 1.00 | 1.03 | 1.09 | 1.16 | 1.17 | 1.24 |

Moisture uptake=final weight/start weight

Conclusion

Rate of moisture uptake and final moisture uptake per gram device were equivalent for all oxygen formulations. Devices with higher oxygen content weigh less per area, and so absorb fewer total grams water per area.

Example 9

Stability of Oxygen Concentration in Oxygen-Delivery Device Through E-Beam Irradiation The following experiment was conducted in order to test the stability of foamed oxygen devices over time and through e-beam irradiation.

Medical devices must exhibit some level of sterility. A method of sterilization ideal for polyacrylamide is electron beam irradiation. E-beam irradiation potentially could reduce substrates through electron bombardment, and products must be tested for resistance to possible e-beam damage. In addition, the long term oxygen concentration stability of the oxygen-delivery device in packaging must be established. Foil packaging was chosen due to its properties as an oxygen barrier.

Experimental Design
The following steps were followed:
1) Prepare ten 10% foamed oxygen matrices (1% carbonate) as described in Example 8, but the hydrogen peroxide concentration is a 10% solution rather than the typical 3% solution.
2) Package in foil. 11-17-99.
3) Send five to e-beam 11-24-99.

4) Place 0.3 g of e-beamed and control oxygen devices in 600 mL distilled water each in sealed glass bottles, excluding air bubble. 11-29-99
5) At t=24 hrs, read dissolved oxygen.
Results
Sterilization lot#993043 25-33.1 kGy dose PO#624
11-29 E-beam→11.5 ppm
11-29 control oxygen→11.5 ppm
11-29 control ACRYDERM® matrix material→9.0 ppm
Conclusion
E-beam irradiation had no discernable effect on the condition or oxygen concentration of the foamed oxygen-delivery devices. Moreover, devices packaged in foil showed no significant loss of oxygen over a 12 day time period.

Example 10

New Formulations of Oxygen-Delivery Devices

The following experiment was conducted in order to determine alternative oxygen-delivery device formulations to improve general characteristics.

In order to improve several characteristics of the original foamed oxygen matrix, such as flexibility, stability, moisture uptake, or elasticity, certain variables were manipulated. These included catalyst variations and changes in the concentration of key components. A wide range of devices may be manufactured in this manner.
Experimental Design
The following steps were followed:
1) Prepare 8 ACRYDERM® matrix material devices, containing:
   A. 1% sodium carbonate, undried gel
   B. 0.5% sodium carbonate, 0.5% sodium bicarbonate
   C. 1% sodium carbonate, 40% less glycerol than the standard Acryderm matrix
   D. 1% sodium carbonate, 30% less glycerol
   E. 1% sodium carbonate, 50% less glycerol, 50% less guar gum
   F. 1% sodium carbonate, no guar gum
   G. 1% sodium carbonate, 25% more guar gum
   H. 1% sodium carbonate, 0.01% sodium iodide.
The standard matrix composition is described in Example 1 and the carbonate amounts are given in Example 8. Changes described herein are changes from the standard matrix composition.
2) Add 0.25 mL of 20% hydrogen peroxide to 0.6 g each matrix
3) Matrices were observed for foam formation.
Results

| ID | Results |
|---|---|
| A. | very big bubbles, less flexible |
| B. | normal |
| C. | slightly too stiff, not flexible |
| D. | slightly stiff, good |
| E. | stiff, but still good, more clear |
| F. | more flexible, clear, big bubbles |
| G. | non uniform bubbles, lots of smaller bubbles |
| H. | Very quick foam formation, non uniform bubbles |

Conclusion
Changing key components of the ACRYDERM® matrix material batch resulted in different final oxygen levels. Some components, such as guar gum, may not be a necessary component. In fact, a good oxygen-delivery matrix may comprise a flexible, solvent-absorbent polymer, peroxide, and a decomposition catalyst.

Example 11

Oxygen Entrapment in Non-Polyacrylate Substrates

Polyacrylate is a non-resorbable substrate which limits its use to topical or non-implantable applications wherein the matrix can be removed. Numerous other polymerized materials may form closed cell foams to encase oxygen gas but have the added advantage of being biodegradable, i.e., resorbable. The purpose of this experiment was show the feasibility of entrapment of oxygen gas into other substrates.
Experimental Design:
Gelatin, agar and agarose granuals were dissolved in concentrations ranging from 1 to 5 w/w in water by heating. Various samples of the solutions then received sodium carbonate along with guar gum and glycerol before being poured into molds to gel as sheets. After the gels had set they were dehydrated and then re-hydrated with a hydrogen peroxide solution.
Results
All of the samples formed closed cell foam like materials as long as the catalyst was present in the polymer. The results are summarized in the table.

| Polymer Substrate | Concentration | [Guar Gum] | [Glycerol] | Properties |
|---|---|---|---|---|
| Gelatin | 3% | Yes | Yes | Pliable closed cell foam |
| Gelatin | 3% | No | Yes | Pliable closed cell foam |
| Gelatin | 3% | Yes | No | Brittle closed cell foam |
| Gelatin | 1% | Yes | Yes | Very fragile closed cell foam |
| Agar | 5% | Yes | Yes | Pliable closed cell foam |
| Agar | 5% | No | Yes | Pliable closed cell foam |
| Agar | 5% | Yes | No | Brittle closed cell foam |
| Agar | 1% | Yes | Yes | Very fragile closed cell foam |
| Agarose | 5% | Yes | Yes | Pliable closed cell foam |

Conclusion
These experiments showed that a catalyst was incorporated into a biodebradeable matrix to support the degradation of hydrogen peroxide and that polymers other than polyacrylamide polymers could be used. In such a construct, the addition of hydrogen peroxide to the polymerized materials caused the formation of oxygen gas which became entrapped within the polymer scaffold to form a closed cell foam.

It should be understood that the foregoing relates only to preferred embodiments of the present invention and that numerous modifications or alterations may be made therein without departing from the spirit and the scope of the invention as set forth in the appended claims.

What is claimed is:
1. An oxygen-delivery wound treatment device comprising closed cells and walls, the device comprising:
   a) a formed biocompatible matrix comprising a swellable, cross-linked polyacrylamide, a non-gellable polysaccharide, and a sodium carbonate catalyst;

b) gaseous oxygen, wherein the gaseous oxygen is contained in the closed cells; and c) dissolved oxygen, wherein the dissolved oxygen is present in moisture in the walls, wherein the gaseous oxygen and the dissolved oxygen are produced when hydrogen peroxide is reacted with the sodium carbonate catalyst.

2. The matrix of claim 1, further comprising at least one active agent.

3. The matrix of claim 1, wherein the matrix comprises a stranded configuration.

4. The matrix of claim 1, further comprising a water loss control agent comprising petrolatum, glycolipids, ceramides, free fatty acids, cholesterol, triglycerides, sterylesters, cholesteryl sulfate, linoleic ethyl ester, or silicone oil.

5. The matrix of claim 1, further comprising a plasticizer comprising glycerol, water, propylene glycol, or butanol.

6. The matrix of claim 1, further comprising a hydration control agent comprising isopropyl alcohol, ethanol, glycerol, butanol, or propylene glycol.

7. The matrix of claim 1, wherein the non-gellable polysaccharide is guar gum.

8. An oxygen delivery wound treatment device comprising closed cells and walls, the device comprising;

a) a formed biocompatible matrix comprising a swellable, cross-linked polyacrylamide, a non-gellable polysaccharide, and a sodium carbonate catalyst;

b) gaseous oxygen, wherein the gaseous oxygen is contained in the closed cells, c) dissolved oxygen, wherein the dissolved oxygen is present in moisture in the walls, wherein the gaseous oxygen and the dissolved oxygen are produced when hydrogen peroxide is reacted with the sodium carbonate catalyst; and d) at least one active agent.

9. The matrix of claim 8, wherein the matrix comprises a stranded configuration.

10. The matrix of claim 8, further comprising a water loss control agent comprising petrolatum, glycolipids, ceramides, free fatty acids, cholesterol, triglycerides, sterylesters, cholesteryl sulfate, linoleic ethyl ester, or silicone oil.

11. The matrix of claim 8, further comprising a plasticizer comprising glycerol, water, propylene glycol, or butanol.

12. The matrix of claim 8, further comprising a hydration control agent comprising isopropyl alcohol, ethanol, glycerol, butanol, or propylene glycol.

13. The matrix of claim 8, wherein the non-gellable polysaccharide is guar gum.

* * * * *